(12) United States Patent
Köhler et al.

(10) Patent No.: US 9,986,916 B2
(45) Date of Patent: Jun. 5, 2018

(54) CATHETER COMPRISING CAPACITIVE MICROMACHINED ULTRASONIC TRANSDUCERS WITH AN ADJUSTABLE FOCUS

(75) Inventors: Max Oskar Köhler, Espoo (FI); Peter Dirksen, Valkenswaard (NL); Shunmugavelu Sokka, Eindhoven (NL); Ronald Dekker, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 831 days.

(21) Appl. No.: 13/885,791

(22) PCT Filed: Nov. 15, 2011

(86) PCT No.: PCT/IB2011/055095
§ 371 (c)(1),
(2), (4) Date: Sep. 3, 2013

(87) PCT Pub. No.: WO2012/066477
PCT Pub. Date: May 24, 2012

(65) Prior Publication Data
US 2014/0005521 A1    Jan. 2, 2014

(30) Foreign Application Priority Data

Nov. 18, 2010 (EP) ..................... 10191647

(51) Int. Cl.
*A61B 8/08* (2006.01)
*A61B 8/12* (2006.01)
(Continued)

(52) U.S. Cl.
CPC .............. *A61B 5/015* (2013.01); *A61B 5/055* (2013.01); *A61B 5/064* (2013.01); *A61B 5/4836* (2013.01);
(Continued)

(58) Field of Classification Search
CPC ............ A61N 7/022; A61N 2007/0052; A61B 8/0841; A61B 6/03
(Continued)

(56) References Cited

U.S. PATENT DOCUMENTS 5,980,461 A * 11/1999 Rajan ..................... A61B 8/08
600/459
6,309,355 B1 * 10/2001 Cain ................ A61B 17/22004
600/439
(Continued)

FOREIGN PATENT DOCUMENTS

WO    2006026459 A2    3/2006
WO    2009037655 A2    3/2009
(Continued)

OTHER PUBLICATIONS

International Society for Therapeutic Ultrasound 2009 Final Program.
(Continued)

*Primary Examiner* — Timothy J Neal

(57) ABSTRACT

A catheter (700, 800, 1206) includes a shaft with distal (808, 906, 1004, 208) and proximal ends (1006). The distal end comprises at least one array of capacitive micromachined ultrasound transducers (308, 402, 404, 500, 512, 600, 604, 802, 008) with an adjustable focus for controllably heating a target zone (806, 1014, 1210). A connector (1012) at the proximal end supplies the at least one array of capacitive micromachined ultrasound transducers with electrical power and controls the adjustable focus.

20 Claims, 12 Drawing Sheets

(51) Int. Cl.
| | |
|---|---|
| A61B 5/01 | (2006.01) |
| A61N 7/02 | (2006.01) |
| B06B 1/02 | (2006.01) |
| A61B 5/055 | (2006.01) |
| A61B 5/00 | (2006.01) |
| A61B 6/03 | (2006.01) |
| A61B 6/00 | (2006.01) |
| A61B 5/06 | (2006.01) |
| A61B 6/12 | (2006.01) |
| A61B 8/00 | (2006.01) |
| A61B 18/00 | (2006.01) |
| A61N 7/00 | (2006.01) |
| A61B 90/00 | (2016.01) |

(52) U.S. Cl.
CPC .............. *A61B 6/03* (2013.01); *A61B 6/4057* (2013.01); *A61B 8/0841* (2013.01); *A61B 8/12* (2013.01); *A61B 8/54* (2013.01); *A61N 7/022* (2013.01); *B06B 1/0292* (2013.01); *A61B 6/12* (2013.01); *A61B 8/445* (2013.01); *A61B 8/4488* (2013.01); *A61B 8/58* (2013.01); *A61B 2018/00023* (2013.01); *A61B 2090/064* (2016.02); *A61B 2090/374* (2016.02); *A61B 2562/028* (2013.01); *A61N 2007/0095* (2013.01)

(58) Field of Classification Search
USPC .................. 600/127, 129, 167, 427, 439
See application file for complete search history.

(56) References Cited

U.S. PATENT DOCUMENTS

| | | | | |
|---|---|---|---|---|
| 6,428,477 | B1* | 8/2002 | Mason | A61N 7/02 600/437 |
| 6,461,314 | B1 | 10/2002 | Pant | |
| 6,469,957 | B1* | 10/2002 | Savord | G01N 29/346 367/137 |
| 6,547,735 | B1* | 4/2003 | Henderson | A61B 8/14 128/916 |
| 6,613,005 | B1* | 9/2003 | Friedman | A61N 7/02 600/371 |
| 7,591,794 | B2 | 8/2009 | Lacoste et al. | |
| 7,896,821 | B1* | 3/2011 | Magnin | A61H 23/0245 601/2 |
| 2001/0041163 | A1* | 11/2001 | Sugita | A61K 31/353 424/9.5 |
| 2002/0010502 | A1* | 1/2002 | Trachtenberg | A61F 7/123 607/102 |
| 2003/0216721 | A1 | 11/2003 | Diederich | |
| 2003/0236443 | A1* | 12/2003 | Cespedes | A61B 5/01 600/29 |
| 2005/0200241 | A1* | 9/2005 | Degertekin | G01N 29/2406 310/334 |
| 2006/0085049 | A1* | 4/2006 | Cory | A61B 5/0536 607/48 |
| 2006/0184069 | A1* | 8/2006 | Vaitekunas | A61N 7/02 601/2 |
| 2006/0264758 | A1* | 11/2006 | Hossack | A61B 8/0841 600/467 |
| 2007/0013269 | A1* | 1/2007 | Huang | B06B 1/0292 310/334 |
| 2007/0106157 | A1 | 5/2007 | Kaczkowski | |
| 2007/0129633 | A1* | 6/2007 | Lee | A61B 8/12 600/439 |
| 2008/0154132 | A1 | 6/2008 | Hall et al. | |
| 2008/0177180 | A1* | 7/2008 | Azhari | A61B 8/0825 600/439 |
| 2008/0221448 | A1 | 9/2008 | Khuri-Yakub | |
| 2009/0079299 | A1* | 3/2009 | Bradley | G01S 15/8925 310/322 |
| 2009/0221902 | A1 | 9/2009 | Myhr | |
| 2009/0264759 | A1* | 10/2009 | Byrd | A61B 8/0883 600/445 |
| 2010/0016764 | A1* | 1/2010 | Lacoste | A61N 7/02 601/2 |
| 2010/0056916 | A1 | 3/2010 | Bakker | |
| 2010/0063422 | A1* | 3/2010 | Hynynen | A61B 8/546 601/2 |
| 2010/0168572 | A1 | 7/2010 | Sliwa et al. | |
| 2010/0262014 | A1 | 10/2010 | Huang | |
| 2010/0280388 | A1* | 11/2010 | Huang | A61B 8/12 600/459 |
| 2011/0077637 | A1* | 3/2011 | Brannan | A61B 18/18 606/33 |
| 2011/0172659 | A1* | 7/2011 | Brannan | A61B 18/1477 606/42 |
| 2011/0201973 | A1* | 8/2011 | Stephens | A61B 8/08 601/2 |
| 2012/0010528 | A1 | 1/2012 | Dirksen | |
| 2012/0010538 | A1 | 1/2012 | Dirksen | |

FOREIGN PATENT DOCUMENTS

| | | | | |
|---|---|---|---|---|
| WO | | 2009073748 A1 | 6/2009 | |
| WO | WO/2009073748 A1 * | | 6/2009 | ............... A61B 8/06 |
| WO | | 2009125002 A1 | 10/2009 | |

OTHER PUBLICATIONS

Wong, Serena H. et al "Capacitive Micromachines Ultrasounic Transducers for High Intensity Focused Ablation of Upper Abdominal Tumors", 2006 IEEE Ultrasonics Symposium, pp. 841-844.

Lou, Cunguang et al "Temperature Monitoring Utilizing thermoacoustic Signals during Pulsed Microwave Thermotherapy: A Feasibility Study", Int. F. Hyperthermia, Jun. 2010, vol. 26, No. 4, pp. 338-346.

Lafon, Cyril et al "Feasibility of Haemostasis in Prostate using a Flat Trans-Urethral Transducer", 2003 IEEE Ulrasonics Symposium—pp. 829-832.

Arthur, R.M. et al "Non-Invasive Estimation of Hyperthermia Temperatures with Ultrasound" Int. F. Hyperthermia, Sep. 2005, vol. 21, No. 6, pp. 589-600.

Liu, Dalong et al "Real-Time 2-D Temperature Imaging Using Ultrasound" IEEE Transaction on Biomedical Engineering, vol. 57, No. 1, Jan. 2010.

Pramanik, Manojit et al "Thermoacoustic and Photoacoustic Sensing of Termperature", Journal of Biomedical Optics, vol. 14, No. 5, Sep. 2009.

Rivens, I. et al "Treatment Monitoring and Thermometry for Therapeutic Focused Ultrasound", Int. F. Hyperthermia, Mar. 2007, vol. 23, No. 2, pp. 121-139.

Wang, Yunqiu et al "Semiautomatic Three-Dimensional Segmentation of the Prostate using Two-Dimensional Ultrasound Images", Med. Phys. vol. 30, No. 5, May 2003, pp. 887-897.

Ergun, A. Sanli et al "Finite Element Analysis of Capacitive Micromachined Ultrasonic Transducers", IEEE Transactions on Ultrasonics, Ferroelectrics, and Frequency Control, vol. 52, No. 12, Dec. 2005.

Ross, Anthony B. et al "Highly Directional Transurethral Ultrasound Applicators with Rotational Control for MRI-Guided Prostatic Thermal Therapy", Physics in Medicine and Biology, vol. 49, 2004, pp. 189-204.

Chopra, R., N. Baker, V. Choy, A. Boyes, K. Tang, D. Bradwell, and M. J. Bronskill. 2008. "MRI-compatible transurethral ultrasound system for the treatment of localized prostate cancer using rotational control" Med.Phys. 35:1346-1357.

Chopra, R., M. J. Bronskill, M. A. Haider, and L. Klotz. 2010. "Preliminary human evaluation of MRI-guided transurethral ultrasound therapy for the treatment of localized prostate cancer" ISMRM, 18th Annual Meeting 529.

Chopra, R., M. Burtnyk, M. A. Haider, and M. J. Bronskill. 2005. "Method for MRI-guided conformal thermal therapy of prostate with planar transurethral ultrasound heating applicators" Phys.Med. Biol. 50:4957-4975.

(56) References Cited

OTHER PUBLICATIONS

Diederich, C. J., W. H. Nau, A. B. Ross, P. D. Tyreus, K. Butts, V. Rieke, and G. Sommer. 2004. "Catheter-based ultrasound applicators for selective thermal ablation: progress towards MRI-guided applications in prostate" Int.J. Hyperthermia 20:739-756.

Diederich, C. J., R. J. Stafford, W. H. Nau, E. C. Burdette, R. E. Price, and J. D. Hazle. 2004. "Transurethral ultrasound applicators with directional heating patterns for prostate thermal therapy: in vivo evaluation using magnetic resonance thermometry" Med.Phys. 31:405-413.

Gelet, A., J. Y. Chapelon, R. Bouvier, O. Rouviere, Y. Lasne, D. Lyonnet, and J. M. Dubernard. 2000. "Transrectal high-intensity focused ultrasound: minimally invasive therapy of localized prostate cancer" J.Endourol. 14:519-528.

Haider, M. A., L. Klotz, M. J. Bronskill, K Siddiqui, A. Colquhoun, L. Sugar, and R. Chopra. 2010. "MRI-guided transurethral ultrasound therapy with real-time feedback—a human study" ISMRM, 18th Annual Meeting p. 475.

Hutchinson, E. B. and K. Hynynen. 1998. "Intracavitary ultrasound phased arrays for prostate thermal therapies: MRI compatibility and in vivo testing" Med.Phys. 25: p. 2392-2399.

Kinsey, A. M., C. J. Diederich, V. Rieke, W. H. Nau, K. B. Pauly, D. Bouley, and G. Sommer. 2008. "Transurethral ultrasound applicators with dynamic multi-sector control for prostate thermal therapy: in vivo evaluation under MR guidance" Med.Phys. 35:2081-2093.

Pauly, K. B., C. J. Diederich, V. Rieke, D. Bouley, J. Chen, W. H. Nau, A. B. Ross, A. M. Kinsey, and G. Sommer. 2006. "Magnetic resonance-guided high-intensity ultrasound ablation of the prostate" Top.Magn Reson Imaging 17: p. 195-207.

Pijnenburg, R. H. W., R. Dekker, C. C. S. Nicole, A. Aubry, and E. H. E. C. Eummelen. 2004. "Integrated micro-channel cooling in silicon" Solid state device research conference, 34th Annual Meeting p. 129-132.

Ross, A. B., C. J. Diederich, W. H. Nau, V. Rieke, R. K. Butts, G. Sommer, H. Gill, and D. M. Bouley. 2005. "Curvilinear transurethral ultrasound applicator for selective prostate thermal therapy" Med.Phys. 32: p. 1555-1565.

Sahn, D. J., D. N. Stephens, J. M. Cannata, K. Shung, O. Oralkan, A. Nikoozadeh, B. T. Khuri-Yakub, H. Nguyen, P. Chen, A. M. Dentinger, D. Wildes, K. E. Thomenius, A. Mahajan, K. Shivkumar, and M. O'Donnell. 2009. "A family of intracardiac ultrasound imaging devices designed for guidance of electrophysiology ablation procedures" Conf.Proc. IEEE Eng Med.Biol.Soc. 2009: p. 1913-1917.

Sanghvi, N. T., R. S. Foster, R. Bihrle, R. Casey, T. Uchida, M. H. Phillips, J. Syrus, A. V. Zaitsev, K. W. Marich, and F. J. Fry. 1999. "Noninvasive surgery of prostate tissue by high intensity focused ultrasound: an updated report" Eur.J. Ultrasound 9: p. 19-29.

Wong, S. H., M. Kupnik, R. D. Watkins, K. Butts-Pauly, and B. T. Khuri-Yakub. 2010. "Capacitive micromachined ultrasonic transducers for therapeutic ultrasound applications" IEEE Trans.Biomed. Eng 57: p. 114-123.

\* cited by examiner

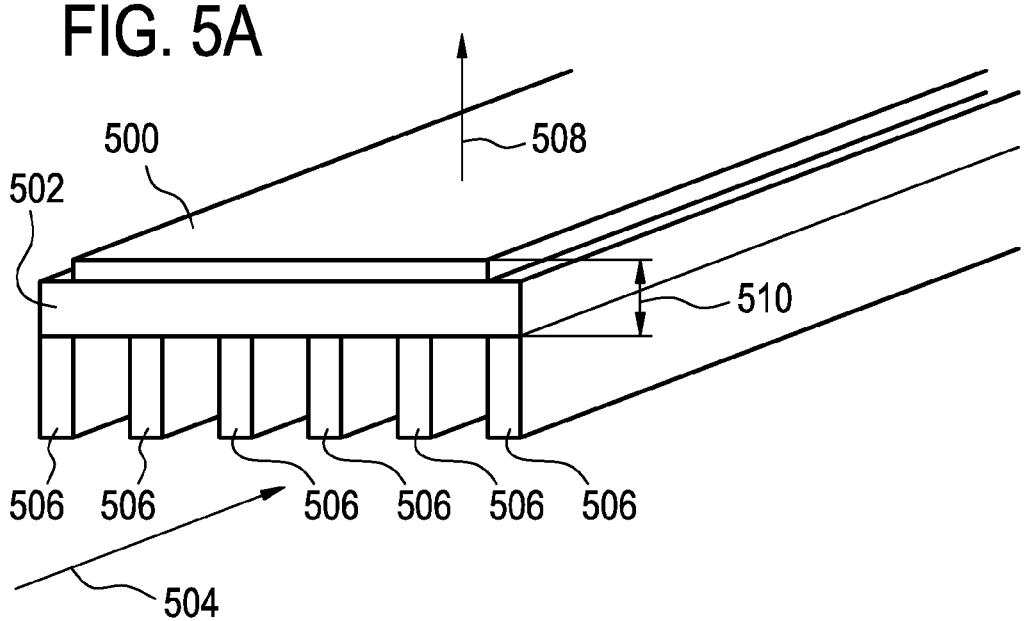
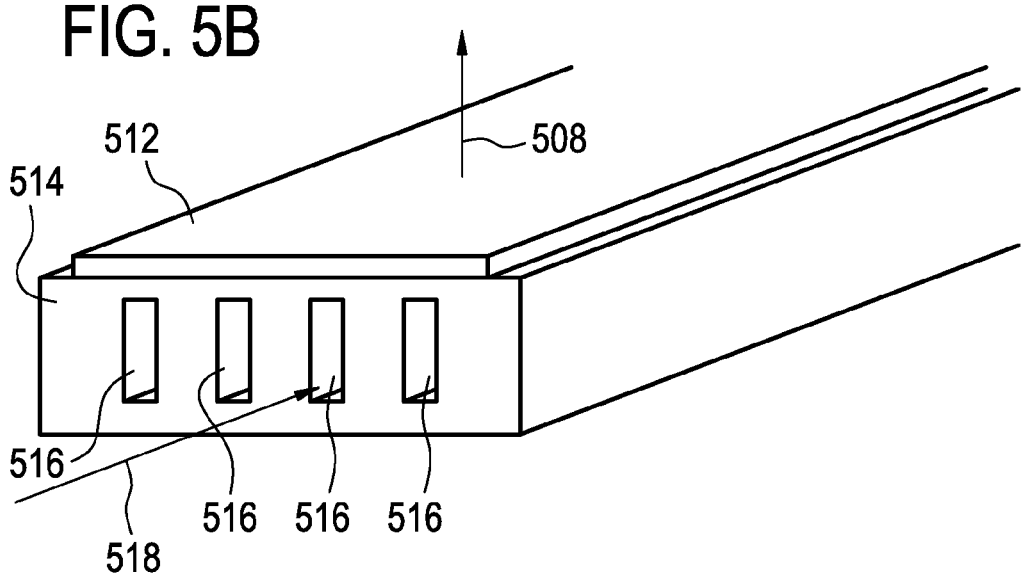

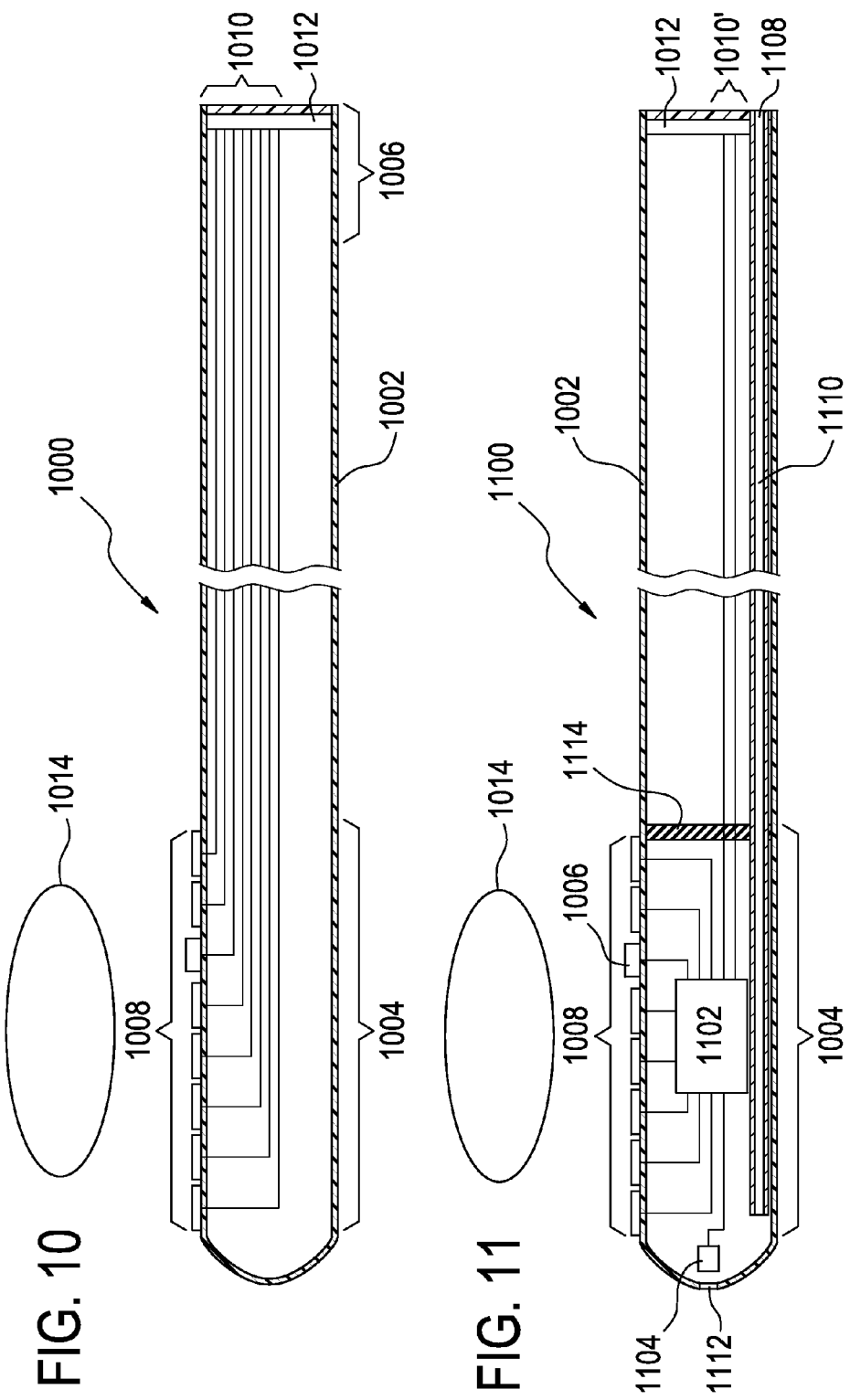

US 9,986,916 B2

CATHETER COMPRISING CAPACITIVE MICROMACHINED ULTRASONIC TRANSDUCERS WITH AN ADJUSTABLE FOCUS

CROSS-REFERENCE TO PRIOR APPLICATIONS

This application is the U.S. National Phase application under 35 U.S.C. § 371 of International Application No. PCT/IB2011/055095, filed on Nov. 15, 2011, which claims the benefit of European Patent Application No. 10191647.6, filed on Nov. 18, 2010. These applications are hereby incorporated by reference herein.

TECHNICAL FIELD

The invention relates to catheters for heating a target volume of a subject with ultrasonic energy, in particular the invention relates to the use of capacitive micromachined ultrasonic transducers for generating the ultrasound and the use of medical imaging for controlling the focus of the generated ultrasound.

BACKGROUND OF THE INVENTION

High-intensity focused ultrasound (HIFU) ablation of the prostate has conventionally been done through the rectal wall with a transrectal probe. Alternatively, ablation can also be done through the wall of the urethra using a transurethral probe. The transurethral approach has several safety-related advantages as compared to the transrectal approach. Because the location of the urethra is known (probe within urethra), it is easier to avoid unintentional thermal damage to the urethra that might increase the risk of incontinency. Moreover, since there is no sonication through the rectal wall, the risk of damaging this sensitive structure is also significantly reduced. The main disadvantage of the transurethral approach is that the space available for the transducer is substantially reduced as compared to the transrectal approach. This basically limits the catheter transducer design to one dimensional phased arrays if employing conventional piezoceramic or piezocomposite transducers, thus also limiting the possible sonication methods that can be used. For practical reasons, traditional transducers are ridged with a relative low number of large elements, arranged in a row, i.e. a linear (one dimensional) array.

In Ergun et. al, IEEE Transactions on Ultrasonics, Ferroelectrics, and Frequency Control, Vol. 52, pp. 2242-2258 (2005) the fabrication and use of capacitive micromachined ultrasonic transducers for imaging is reviewed.

The US-patent application US 2008/0221448 mentions a catheter with an annular array of capacitive micromachined ultrasound transducers for real time forward looking acoustic imaging with a HIFU device for tissue ablation.

SUMMARY OF THE INVENTION

The invention provides for a catheter, a medical imaging system, a computer program product, and a method in the independent claims. Embodiments are given in the dependent claims. The catheter of the invention is provided with a transducer module of one or more capacitive micromachined transducer arrays. According to the invention the transducer module is at least partly deformable.

For transurethral HIFU ablation in particular, capacitive micromachined ultrasound transducers (CMUTs) offer an interesting alternative to piezocomposite transducers. CMUTs allow a substantial reduction in transducer diameter while still allowing a two dimensional phased array due to the very small size of the elements. The two dimensional phased array also allows a formation of a focus, which in turn allows for more accurate and safer ablation procedure as borders of the target tissue can be followed more carefully. However, the number of elements perpendicular to the catheter is low, which results in a relative broad focus in that direction. So, the resolution or beam size in X and Y will not be equal. CMUTs are furthermore cheaper than conventional piezoceramic or piezocomposite transducers and can be made lead free, which allows these CMUTs to be disposable. This is a significant advantage for HIFU therapies using intracavitary transducers, as is the case for both transurethral and transrectal HIFU ablation of the prostate. In addition, silicon transducers can be made flexible, however conventional piezo crystals are not flexible. That is at least a portion of the at least one array of the capacitive micromachined ultrasound transducers is flexible.

HIFU ablation of the prostate has been mainly done using transrectal ultrasound probes, since this gives a larger freedom in the transducer design. However, ablation of the entire prostate gland is difficult (especially anterior wall), and the protection of non-targeted tissues such as the urethra and rectal wall are also challenging.

A 'capacitive micromachined ultrasonic transducer' (CMUT) as used herein encompasses a capacitive ultrasound transducer that has been manufactured using micromachining technologies. Micromachining technologies are thin film manufacturing techniques; typically they are performed using processes identical to or similar to those used for manufacturing integrated circuits.

Recent developments have led to the prospect that medical ultrasound transducers can be manufactured by semiconductor processes. These processes may be the same ones used to produce the circuitry needed by an ultrasound probe such as a CMOS process. These developments have produced micromachined ultrasonic transducers or MUTs. MUTs have been fabricated in two design approaches, one using a semiconductor layer with piezoelectric properties (PMUTs) and another using a diaphragm and substrate with electrode plates that exhibit a capacitive effect (CMUTs). The CMUT transducers are tiny diaphragm-like devices with electrodes that convert the sound vibration of a received ultrasound signal into a modulated capacitance. For transmission the capacitive charge applied to the electrodes is modulated to vibrate the diaphragm of the device and thereby transmit a sound wave. Since these devices are manufactured by semiconductor processes the devices generally have dimensions in the 10-200 micron range, but can range up to device diameters of 300-500 microns. Many such individual CMUTs can be connected together and operated in unison as a single transducer element. For example, four to sixteen CMUTs can be coupled together to function in unison as a single transducer element. A typical two dimensional transducer array currently may have 2000-3000 piezoelectric transducer elements. When fabricated as a CMUT array, over one million CMUT cells may be used. Surprisingly, early results have indicated that the yields, from a semiconductor fabrication plant, of CMUT arrays of this size should be markedly improved over the yields for lead zirconate titanate (PZT) arrays of several thousand transducer elements.

A pre-collapsed capacitive ultrasonic transducer as used herein encompasses a capacitive micromachined ultrasonic transducer that is normally in a collapsed state.

CMUTs were initially produced to operate in what is now known as an "uncollapsed" mode. A typical uncollapsed CMUT transducer cell is fabricated along with a plurality of similar adjacent cells on a substrate such as silicon. A diaphragm or membrane which may be made of silicon nitride is supported above the substrate by an insulating support which may be made of silicon oxide or silicon nitride. The cavity between the membrane and the substrate may be air or gas-filled or wholly or partially evacuated. A conductive film or layer such as gold forms an electrode on the diaphragm, and a similar film or layer forms an electrode on the substrate. These two electrodes, separated by the dielectric cavity, form a capacitance. When an acoustic signal causes the membrane to vibrate the variation in the capacitance can be detected, thereby transducing the acoustic wave into a corresponding electrical signal. Conversely, an A.C. signal applied to the electrodes may modulate the capacitance, causing the membrane to move and thereby transmit an acoustic signal.

Due to the micron-size dimensions of a typical CMUT, numerous CMUT cells are typically fabricated in close proximity to form a single transducer element. The individual cells can have round, rectangular, hexagonal, or other peripheral shapes. A CMUT cell may also be referred to as: a capacitive micromachined ultrasound transducer cell, a capacitive micromachined ultrasound transducer, a CMUT element, and a capacitive micromachined ultrasound transducer element.

The CMUT is inherently a quadratic device so that the acoustic signal is normally the harmonic of the applied signal, that is, the acoustic signal may be at twice the frequency of the applied electrical signal frequency. To prevent this quadratic behavior a bias voltage is applied to the two electrodes which cause the diaphragm to be attracted to the substrate by the resulting columbic force. A DC bias voltage VB is applied to a terminal and is coupled to the membrane electrode by a path which poses a high impedance Z to A.C. signals such as inductive impedance. A.C. signals are capacitively coupled to and from the membrane electrode from a signal terminal. The positive charge on the membrane causes the membrane to distend as it is attracted to the negative charge on the substrate 12. The CMUT cell only weakly exhibits the quadratic behavior when operated continuously in this biased state.

It has been found that the CMUT is most sensitive when the membrane is distended so that the two oppositely charged plates of the capacitive device are as close together as possible. A close proximity of the two plates may cause a greater coupling between acoustic and electrical signal energy by the CMUT. Thus it is desirable to increase the bias voltage VB until the dielectric spacing between the membrane and substrate is as small as can be maintained under operating signal conditions. In constructed embodiments this spacing has been on the order of one micron or less. If the applied bias voltage is too great, however, the membrane can contact the substrate, short-circuiting the device as the two plates of the device are stuck together by Van der Waals forces. This sticking can occur when the CMUT cell is overdriven, and can vary from one device to another with the same bias voltage VB due to manufacturing tolerance variations. While permanent sticking can be reduced by embedding the device electrodes in an electrical isolation layer (e.g., silicon nitride), the nonlinearity of operation between collapsed and uncollapsed states is an inherent disadvantage when trying to operate an uncollapsed CMUT in a range of maximal sensitivity.

Even when the membrane is biased to cause a very small sub-micron dielectric spacing, the sensitivity of the CMUT can be less than that which is desired. This is due to the fact that, whereas the charge at the center of the membrane is relatively close to and may move considerably in relation to the opposing charge, the charge at the periphery of the membrane where the membrane is supported by the support may move very little and hence have little participation in the transduction of signals by the device. One approach to eliminating this disparity has been to use a small membrane electrode which does not extend to the supports. This restricts the charge on the membrane electrode to the center of the device where it may participate strongly in the motion of the membrane and hence the transduction by the device. There still must be one or more electrical conductors to apply the bias voltage V to the membrane electrode 20 and to couple the A.C. signals to and from the electrode. These electrical conductors are necessarily very thin, with dimensions that impose undesirably large impedances on the A.C. signals, thereby limiting the sensitivity of the device.

Using a transurethral approach to prostate HIFU ablation makes it easier to spare non-targeted tissues and also makes it easier to ablate the entire gland. Transurethral HIFU probes face an additional difficulty due to the limitation on the size of the ultrasound applicator. Despite of these challenges, one dimensional phased arrays have been recently used for clinical transurethral HIFU ablation of the prostate under guidance of MR thermometry. Conventional planar or curvilinear transurethral phased-array transducers emit ultrasound in one direction only, therefore requiring mechanical rotation to ablate the entire gland. This mechanical rotation may require a long treatment duration to treat the entire gland. A further difficult is that this method of treatment may result in MR artifacts. The MR artifacts occur in part due to the rotation directly and in part due to the long therapy duration imposed by the need for rotation to heat the entire gland. Alternative approaches using multi-sectored tubular transurethral applicators have also been proposed in order to avoid or minimize the need for rotation, thus substantially shortening the treatment time. These transducers do however suffer from a less angular control of the heating due to the less directional acoustic field, which in turn makes it more difficult to spare structures that should not be heated.

The use of catheter CMUTs for transurethral HIFU probes may be beneficial. Utilization of CMUT technology may allow the size of the HIFU probe to be reduced, while still allowing for two dimensional phased-arrays which in turn can be used to obtain a very well-defined beam profile. This would be very useful in order avoid heating sensitive structures such as nerve bundles, thereby reducing the risk of impotency. The higher thermal conductivity of the silicon used in the CMUTs as compared to the piezocomposites used in conventional transducers would also allow higher powers to be emitted with less heating of the applicator and thus less risk of causing excessive heating of the urethra. For a CMUT, the thickness of the transducer can be chosen freely, i.e. the thickness has no impact on the frequency (in contrast to the piezo crystal). This also makes the cooling of the CMUT easier.

The improved cooling would further reduce the risk of incontinency. It is furthermore difficult to create ultrasound with CMUTs at sufficiently low frequencies for externally applied HIFU (transducer external to body) but for the short penetration depth required for transurethral HIFU ablation of the prostate CMUTs would seem ideal. The frequencies typically used in transurethral ultrasound are between 5-8.5

MHz, with larger frequencies being used for more shallow targets due to the improved beam quality and efficient energy absorption at these penetration depths. The advantages are further elaborated below.

The limited amount of elements in traditional piezoceramic or piezocomposite transurethral transducers renders beam formation basically not possible. If the transducer stick is made curvilinear a rather well-defined acoustic pattern can be obtained perpendicularly to the acoustically active surface. However, using CMUTs would allow for two dimensional phased-arrays and consequently full beam steering capabilities. This might require full integration of CMUT on top of CMOS, integration on top of a micro beam former. This would in turn allow for the generation of a focal point or multiple focal points that would be well-defined regions in three dimensions, which could be temporally switched in order to ablate the entire desired volume with minimal heating of nearby tissues that should be spared. However, it may be noted that the focal point may not be symmetrical due to the much larger amount of elements along the transducer probe than perpendicular to the probe. The focal point may therefore be elongated, but the intensity pattern can alternatively be split into multiple more or less symmetrical focal points along the direction of the probe. The use of electronic beam formation and/or beam steering allows not only to more carefully spare tissues such as the nerve bundles but also the urethra since the focus (or foci) can be generated at a distance from the urethra thus reducing the heating at the surface of the urethra. The use of multiple foci or one focus may also reduce the total amount of energy needed to heat the desired parts of the prostate, thereby inherently reducing the risk of causing excessive heating at sensitive tissues even further.

According to the invention, the transducer module is at least partly deformable. That is, the transducer module may be flexible and/or can be bent. For example, the CMUT array(s) may be disposed on a flexible material, i.e. on a flexible substrate. In another example, a flexible element can be provided between two CMUT arrays. Because the transducer module is deformable, the distal end on which the transducer module is mounted can be deformed so as to follow narrow bends in the path through the patient's anatomy. Thus, the catheter of the invention can be more accurately navigated through narrow pathways, such as the patient's urethra.

According to another aspects of the invention, by deformation of the transducer module changes the ultrasound focus of the transducer module. Thus, the adjustable focus is at least partially adjusted mechanically.

Another aspect of the invention is that the ablation catheter containing the CMUT can also be made deformable to mechanically create a focus. This does not exclude the CMUT catheter from being a phased array, and the technologies can be advantageously combined. The radius of curvature can be adapted as part of the therapy planning or during the therapy as a preplanning step. This would further improve the beam profile making for an even more accurate ablation procedure.

The CMUT catheter can also be made flexible or partly flexible (only part of the catheter is flexible while rest is stiff) to make insertion into the prostate via the urethra easier than with catheters which use piezocomposites for an active area. With conventional catheters which use PZT transducers the active part of the PZT transducer is not flexible but the shaft may be. The high flexibility of a CMUT catheter may be enabled using a Flex-to-Foil technology. In the Flex-to-Foil technology the CMUTs are manufactured on a flexible substrate. This flexibility does not need to be passive, but the catheter can advantageously be made steerable. This would furthermore enable sonication into the superior part of the prostate from the bladder, which would allow for new treatment options. This possibility could probably be used to further aid in sparing healthy tissues directly outside of the superior part of the prostate but also healthy tissues within the prostate.

The flex-to-foil technology may be a flexible monolithic integrated circuit comprising: flexible circuit elements, connecting elements between the flexible circuit elements, and a flexible coating covering the flexible circuit elements and connecting elements which comprises at least one layer of a layer material comprising a polymer, wherein the flexible coating acts as a passivating layer, a planarizing layer, and a mechanical support for the flexible circuit elements and the connecting elements. In some embodiments the polymer is chosen from the group of polyimide, polycarbonate, fluorocarbon, polysulphon, epoxide, phenol, melamine, polyester, or their co-polymers. In other embodiments the polymer is chosen from the group of polyimide resins.

Furthermore, the superior heat conduction of the silicon used in the CMUTs as compared to the piezo materials used in conventional transducers make it less probable to overheat the transducer and thus also the urethra. This is a direct property of the CMUT but would nevertheless be particularly useful for the transurethral applicator since an overheating of this applicator would directly lead to burning the urethra, in turn causing severe adverse effects that might include incontinency. One could also utilize direct active water cooling of the CMUT to further reduce the temperature of the transducer probe.

As mentioned above, piezoceramic or piezocomposite transurethral transducers either need rotating to treat the entire prostate gland (linear and curvilinear transducers), or if tubular sectored transducers are used then the acoustic intensity distribution is not as well defined as would be preferred. Segments of planar or curvilinear two dimensional phased-array CMUTs can in contrast used to cover the entire 360° of the transducer or only part thereof. The transducer prove can also be made of two flat two dimensional phased-arrays whose backsides are glued to each other. This can be done using the Flex-to-Foil technology. Combining this with the above mentioned features would enable a catheter which no longer requires rotation, or at least a reduced amount of rotation, to maintain a well defined beam profile in three dimensions. This approach would thus allow for a very rapid ablation of the whole prostate while still allowing sensitive structures to be spared. This could be crucial in order to avoid MR temperature mapping artifacts and potential side effects that might occur from unreliable temperature images. This may also reduce treatment time and thus reduce patient discomfort during treatment. The reduction of treatment time also reduces the magnetic resonance imaging system time required to perform the therapy. This may reduce the cost of the therapy and enable more patients to utilize the magnetic resonance imaging system.

As is the case for any interstitial ultrasound device, one would prefer it to be disposable for hygienic reasons. Since the CMUTs can be made lead free and much cheaper than conventional ultrasound transducers the use of CMUTs for transurethral HIFU transducers is also very beneficial from this point of view.

Due to the small space available it is also difficult to add other sensors to the transurethral catheter. Integrating temperature, pressure and flow sensors into the CMUT catheter would be much easier since the same signal chain can be used in essence. These additional sensors would be of benefit since active cooling of the transducer surface with water is commonly used in order to reduce the heating of the transducer and also the urethra. Integrated active cooling of the transducer catheter is also possible for CMUTs. Controlling the water flow and pressure would further improve the safety of the treatment, as both excessive flow and insufficient flow are undesirable. Monitoring the temperature directly is a further means of risk mitigation for the case of potential excessive heating of the urethra. So, the temperature, pressure or flow sensor could be integrated with the CMUT, as they use the same technology flow and can be integrated on top of a dedicated ASIC.

Send-receive technology can furthermore also be incorporated in the CMUT applicator, thereby allowing for ultrasound imaging as well as HIFU ablation. The catheter can be made either forward or sideward looking or both This has however been suggested for CMUT applicators intended for monitoring of electrophysiology interventions. This might aid in the correct positioning of the ultrasound applicator, which might become more difficult with a steerable transurethral CMUT catheter. This can be achieved using Flex-to-Foil technology.

The Flex-to-Foil technology may be key in enabling many of the above mentioned advantages.

The potential beneficial use of the CMUT for prostate HIFU ablation can be summarized as:

1. Improved beam profile and/or electronic beam steering for a more well defined heating profile enabling a more efficient and safe treatment
2. A general advantage of CMUT vs piezo crystal: there is no 'kerf', i.e. the distance between two transducer elements is basically zero. This result in a better beam quality and less side lobes.
3. Deformable catheter to further improve beam profile and aid in sparing non-targeted tissues. Focal length can be adjusted during treatment to be better suited for both ablation of areas close to transducer as well as regions close to the border of the prostate. Can be realized by for example using Flex-to-Foil technology.
4. The CMUT catheter can be made flexible or partly flexible. This may be used to make a passively flexible catheter which is easier to insert into a subject. This flexibility may also enable a catheter which is steerable to better follow the urethra thus making the insertion of the CMUT catheter probe into the prostate easier. For example, by using Flex-to-Foil technology.
5. A flexible and steerable CMUT catheter also enables sonication of the superior part of the prostate from the bladder. This additional freedom for the therapy could potentially be very beneficial. For example, by using Flex-to-Foil technology.
6. Reduced heating of the urethra since the transducer may more efficiently dissipate heat as compared to conventional transducers. The thickness of the silicon die can also be altered without affecting the frequency, which allows thinner dies to be used that can be more efficiently cooled. Furthermore, active cooling of the channels within the CMUT is also possible to even further reduce the heating of the probe.
7. Full 360° or partial angular coverage, or two-sided (top and bottom of flat transducer) coverage of the transducer probe in order to make rotation of the transducer redundant (or minimal) when combined with the beam steering capabilities of the two dimensional phased-array design. Can be realized by for example using Flex-to-Foil technology.
8. Forward and/or sideward looking CMUT can aid in the accurate positioning of the transducer for prostate ablation.
9. CMUTs are cheaper than conventional piezocomposite transducers and lead-free, and can thus be made disposable which makes them preferable for interstitial transducers such as transurethral, transrectal, transesophagal, intravascular, and intracardiac transducers.
10. Easy integration of additional sensors, such as temperature, pressure and/or flow sensors to e.g. control probe temperature.

In general a capacitive micromachined ultrasound transducer is manufactured by:

A sacrificial etch method to create a free hanging membrane.

Gap (the vertical distance between bottom of the cavity and membrane) typical 300 nm.

Typical membrane diameter is 50 to 300 micron, typical membrane thickness is 1 to 2 micron The metal layers and the sacrificial material is a double layer of Aluminum and Molybdenum, deposited at a relative low temperature of typical 400 degree. Advantage: sloped walls; that is good for step coverage.

Typical thickness Al/Mo: 200/50 nm.

The dielectric layers are low temperature PECVD Oxide-Nitride-Oxide (ONO). The ONO stack has favorable properties and shows little electrical charging.

Thermal anneal: T<400 degree.

Typical thickness ONO: 50/150/50 nm.

Etching method: both dry and wet etching.

Use a so-called critical-point-dry method during the sacrificial etch. There is however an alternative dry etch method available (using XeF2).

Additional considerations when manufacturing a CMUT may be:

By choosing a certain combination of diameter, membrane thickness and gap distance, the CMUT is pre-collapsed. That means that the membrane permanently touches the bottom of the cavity. A pre-collapsed CMUT has advantages over conventional CMUT devices: no hysteresis, easier electronics and better performance.

Manufactured using only low temperature steps and materials (basically Aluminum and Nitride) that are commonly found in a CMOS fabrication plant. This implies that the flow is CMOS backend compatible and thus CMUT can be combined with other sensors on the same silicon die or the CMUT can even be integrated on top of a dedicated ASIC. Examples are (capacitive) pressure sensors, flow or temperature sensors or an ultrasound micro beam former.

There are various options to thin the CMUT dies (with ASIC) to say 50-100 micron or even below: this is good for ultrasound properties (suppression of undesired surface waves) but also for cooling.

The CMUT can be coated with a bio compatible coating such as Parylene-C for (electrical) protection.

The CMUT could also be used to monitor the ablation process: ultrasound monitoring of an RF-ablation process is already being done. It would imply 'send and receive electronics', where an ultrasound measurement is combined with ablation.

CMUTs and the methods outlined could be used irrespective of whether magnetic resonance or ultrasound is used for guidance and thermometry of the HIFU procedure. The invention is even applicable if there is no means of monitoring used at all.

The embodiment of the invention may also be used for non-ablation HIFU, e.g. for extended hyperthermia for localized drug delivery and gene therapy. However, these applications have not yet (at least widely) been reported on for prostate. The invention can be used not only for prostate cancer but also for benign prostate hyperplasia and all other prostate related illnesses that could potentially be treated by thermal ablation, local drug delivery, local gene therapy.

The invention can advantageously be used for any interstitial ultrasound applicator that is used for HIFU ablation or hyperthermia. For example, the catheter CMUT can be inserted into the body through a puncture hole (for ablation of liver in the same way as laser, microwave, and RF applicators are currently inserted), or into any other orifice for ablation or hyperthermia purposes (e.g. cardiac ablation from the esophagus).

The CMUT catheter can also be used for HIFU ablation of tissue anywhere within the bile ducts, or gastrointestinal, vascular or pulmonary system. The CMUT can be inserted and navigated in these systems (insertion probably needs to be percutaneous for the vascular system, and bile ducts), for example by being inserted into a vein and then the flexible transducer probe can be mechanically steered towards the target tissue. The CMUT can for example be used for intracardiac or transesophagal EP ablation for treatment of arrhythmia. This advantage is enabled by the small size of the CMUT catheter. This can be combined with the above advantages such as the 'beacon', thereby allowing for the exact localization or navigation of the CMUT probe within these systems which in turn allows accurate ablation of the potential targets within these systems. The CMUT can also be used for ultrasound imaging within these systems or monitoring of ablation or other therapy, although this is at least in part already disclosed as prior art.

'Medical image data' is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' as used herein encompasses to any device comprising a processor. A processor is an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

A 'user interface' as used herein is an interface which allows a user or operator to interact with a computer or computer system. A user interface may provide information or data to the operator and/or receive information or data from the operator. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of receiving information or data from an operator.

In one aspect the invention provides for a catheter comprising a shaft with distal and proximal ends. The distal end comprises at least one array of capacitive micromachined ultrasound transducers with an adjustable focus for controllably heating a target zone. The catheter further comprises a connector at the proximal end for supplying the at least one array of capacitive micromachined ultrasound transducers with electrical power for controlling the adjustable focus. The use of capacitive micromachined ultrasound transducers is advantageous for such a catheter. This is because the capacitive micromachined ultrasound transducers may be constructed on a smaller size or scale than conventional piezoelectric transducers. This means that for such a catheter a large number of capacitive micromachined ultrasound transducers may be combined into a single catheter. With such a large number of transducers this enables the focusing or control of ultrasound being directed into the target zone. This may be accomplished in several different ways. The capacitive micromachined ultrasound transducers may be physically focused such that their alignment is changed such that the ultrasound converges in a target zone and heats the target zone.

In another embodiment the adjustable focus is at least partially adjusted mechanically. In some embodiments there is a plurality of arrays of capacitive micromachined ultrasound transducers and the adjustable focus is at least partially adjusted by mechanically adjusting the relative position between the plurality of arrays of capacitive micromachined ultrasound transducers. In some embodiments the adjustable focus is at least partially controlled by flexing or bending the at least one array of capacitive micromachined ultrasound transducers.

In another embodiment the capacitive micromachined ultrasound transducers the phase and/or amplitude of electrical power supplied to them is controlled. This enables an electronic control of the at least one array of capacitive micromachined ultrasound transducers. In some embodiments there is both mechanical and electrical focusing of the ultrasound.

In another embodiment the adjustable focus is at least partially adjusted by electronic control of the at least one array of capacitive micromachined ultrasound transducers. As used herein the term electronic control encompasses the control of the phase and/or amplitude of alternating current electric power supplied to a capacitive micromachined ultrasound transducer. This may include controlling the amplitude and/or phase to a particular array of capacitive micromachined ultrasound transducers. It may include controlling the phase and/or amplitude to the individual capacitive micromachined transducers which make up an array of capacitive micromachined ultrasound transducers. If a sufficiently large number of capacitive micromachined ultrasound transducers are used, then the focus of the at least one array of capacitive micromachined ultrasound transducers can be shifted. This may be accomplished by controlling the phase and/or amplitude of alternating current electrical power supplied to the transducers.

In another embodiment the distal end comprises at least one integrated circuit for powering the at least one array of capacitive micromachined ultrasound transducers. In some embodiments more than one integrated circuit may be used for powering an array or arrays of capacitive micromachined ultrasound transducers.

In another embodiment the distal end comprises at least one integrated circuit for powering the at least one array of capacitive micromachined ultrasound transducers and for providing electronic control of the adjustable focus. The catheter further comprises a data bus between the at least one integrated circuit and the connector. This embodiment is particularly advantageous because if there are several hundred different capacitive micromachined ultrasound transducers it would not be practical to have a lead for each transducer going to the connector. This would make the catheter prohibitively big. An integrated circuit can be used which can drive individual capacitive micromachined ultrasound transducers or can be used to drive groups or arrays of capacitive micromachined ultrasound transducers. The integrated circuit could be supplied with the power externally via the connector at the proximal end and there could also be a data line which is used to send or receive instructions to the integrated circuit. For instance encoded instructions for performing a sonication using the catheter could be sent to the integrated circuit. In some embodiments the power cable and the data bus are incorporated together. For instance DC power may be supplied along the data bus in some embodiments. A higher frequency data could be transmitted along the same wires.

In another embodiment the at least one integrated circuit comprises circuitry for performing ultrasound imaging using the at least one array of capacitive micromachined ultrasound transducers while heating the target zone. The ultrasound imaging may in some embodiments be performed onboard in the integrated circuit. In other embodiments the data acquired from the capacitive micromachined ultrasound transducers may be sent out on the data bus. The circuitry for performing ultrasound imaging may, in some embodiments, be simply for performing data collection. The reconstruction or the interpretation of the data acquired from the catheter during performing the ultrasound imaging may then be reconstructed by a processor or a computer system externally. In some embodiments the sonication and the ultrasound imaging occur simultaneously. Some capacitive micromachined ultrasound transducers could be driven at a first frequency for performing the sonication and other ultrasound transducers could be driven at a second frequency for performing imaging. In this way the imaging and the heating or sonication of the target zone could be performed simultaneously. In other embodiments the imaging and the heating of the target zone are performed by alternating the two. This embodiment is particularly advantageous because ultrasound imaging may be used for measuring the effectiveness of the heating of the target zone and may also be used for an input to an algorithm for controlling where the catheter heats.

In another embodiment the distal end has a length extension. The distal end has a length extension and a tip. The tip is the end of the catheter and an axis along the shaft would pass through a portion of the tip. The length extension is a region of the distal end which forms a surface surrounding the axis along the shaft. The length extension may alternatively be described as a side portion or region of the distal end. At least a portion of at least one array of capacitive micromachined ultrasound transducers is oriented such that the target zone is located adjacent to the length extension. Worded alternatively, at least one array of capacitive micromachined ultrasound transducers is oriented such that an area to the side of the catheter is heated.

In another embodiment at least some of the at least one array of capacitive micromachined ultrasound transducers form a ring around the shaft. Worded alternatively, at least some of the capacitive micromachined ultrasound transducers form a path or circuit surrounding the length extension. This enables the catheter to heat a target zone or ring surrounding the catheter. This may be used to simultaneously heat in a 360 degree ring around the catheter, it may also enable the catheter to be inserted into a subject and then to selectively decide in which direction to heat. For instance only a portion of the capacitive micromachined ultrasound transducers may be supplied with power. This could be used to control which region of the subject is heated. For instance the catheter could be inserted into the subject and then the direction in which the catheter heats is electronically controlled. This would eliminate the need for mechanically turning the catheter to heat a specific region. The ability of sideways transmission of ultrasound radiation achieves that a wide angular range around the distal end of the catheter can be irradiated without the need for movement or rotation of the catheter. The feature of the sideways transmission functions independently from the flexibility of the array of the capacitive micromachined ultrasound transducers.

In another embodiment at least a portion of the at least one array of capacitive micromachined ultrasound transducers is flexible. In this particular embodiment the array of capacitive micromachined ultrasound transducers is formed on a flexible material. This is extremely advantageous because the catheter may be more easily inserted into a subject. This also enables the bending or flexing of the catheter by a mechanical system to mechanically focus the ultrasound energy generated into a focus which is located at a target zone.

In another embodiment the catheter comprises at least two arrays of capacitive micromachined ultrasound transducers. The catheter further comprises a flexible element between the at least two capacitive micromachined ultrasound transducers. This embodiment is advantageous because it allows the catheter to be flexible. A larger number of capacitive micromachined ultrasound transducers may be incorporated into a catheter because it is flexible. If a catheter were too rigid it may not be able to be inserted into a subject in some situations. A further advantage is that the inclusion of a flexible element allows the at least two arrays of capacitive micromachined ultrasound transducers to direct ultrasound in a different direction. This enables the use of a mechanical system for actuating the at least two arrays of capacitive micromachined ultrasound transducers relative to each other. This may enable an adjustable focus for controlling the heating of the target zone via mechanical means.

In another embodiment the catheter further comprises a mechanical actuator for at least partially adjusting the adjustable focus by flexing the distal end. This embodiment may apply to the embodiment where the catheter comprises at least two arrays of capacitive micromachined ultrasound transducers with a flexible element between them as well as the embodiment where the array of capacitive micromachined ultrasound transducers is flexible. This embodiment also applies to when there is a flexible element and the array of capacitive micromachined ultrasound transducers is flexible. This embodiment is particularly advantageous because the use of the mechanical actuator enables the adjustment of the adjustable focus.

In another embodiment the connector comprises a fluid cooling inlet at the proximal end. The catheter is adapted for supplying the distal end with cooling fluid from the fluid cooling inlet. In some embodiments the cooling fluid drains out of the catheter. In other embodiments a tube is used to direct heated cooling fluid back to the connector. This embodiment is particularly advantageous because the cooling fluid may be used to prevent the at least one array of capacitive micromachined ultrasound transducers from heating to the point where they may cause tissue damage in the subject. For instance in sonicating the prostate gland heating the urethra too much may result in incontinence. The use of cooling fluid may prevent this. Also using cooling fluid allows the capacitive micromachined ultrasound transducers to be used at a higher power rate.

In another embodiment the catheter further comprises a pressure sensor for measuring cooling fluid pressure in the distal end. This embodiment may be advantageous because the pressure sensor may be used for measuring cooling fluid flow at the distal end and it may also be used to ensure that the cooling fluid is not causing too large of a pressure. For instance if the cooling fluid is draining out of a tip of the catheter then it would be advantageous to ensure that too high of a pressure in the subject is not created due to the cooling fluid.

In another embodiment the catheter further comprises a flow sensor for measuring cooling fluid flow. This embodiment is advantageous because the cooling fluid flow directly at the tip may be measured and may be used to ensure that the cooling is functioning properly.

In another embodiment the catheter further comprises both a pressure sensor and a flow sensor. When a flow sensor is incorporated into the catheter it may be incorporated at the tip or within the shaft.

In another embodiment the catheter further comprises a temperature sensor. One or more temperature sensors may be incorporated into the catheter. If cooling fluid is used, temperature sensors at the inlet and outlet for the cooling fluid may be used to measure of the heat dissipated in the catheter. The measure of this heat dissipation may be measured and controlled. Control could be performed by an external computer or control system or by an integrated circuit or controller integrated into the catheter.

In another embodiment the catheter further comprises a temperature sensor for monitoring a temperature of the distal end. This embodiment is particularly advantageous because the temperature in the vicinity of the at least one array of capacitive micromachined ultrasound transducers may be measured directly. This may be used to ensure that a subject is not damaged or hurt by too high a temperature achieved by the ultrasound transducers. The temperature sensor may be a separate sensor that is integrated into the distal end. In other embodiments the temperature sensor may be built directly into the same substrate that the capacitive micromachined ultrasound transducer is manufactured into. For instance a thermistor could be incorporated directly into the process flow which was used during fabrication of the capacitive micromachined ultrasound transducers. Such an embodiment would be advantageous because multiple temperature sensors could be incorporated directly into the area where the ultrasound transducers are located. This would further ensure that even a region of the ultrasound transducers does not become overheated.

With any of the aforementioned sensors the sensor may in some embodiments be connected to an integrated circuit. Any data bus which is between the integrated circuit and the connector may then also be used for relaying data acquired from a sensor.

In another embodiment the shaft comprises a mechanical steering apparatus for steering the distal end. This embodiment is advantageous because a mechanical system may be incorporated into the catheter which allows its position to be adjusted via the mechanical steering apparatus. The mechanical steering apparatus may for instance include elements for twisting the position of the distal end and/or for a bend and flex in particular directions since the catheter may incorporate a pivot and there may be one or more flexible elements which connect rigid elements or semi-rigid elements of the catheter. A system of cables or thin wires may be used then to manipulate the distal end and for steering it using the mechanical steering apparatus.

In another embodiment the capacitive micromachined ultrasound transducers are pre-collapsed capacitive micromachined ultrasound transducers.

In another aspect the invention provides for a medical imaging system for acquiring medical image data from an imaging zone. The medical imaging system comprises a catheter interface for connecting to the connector of a catheter according to an embodiment of the invention. The medical imaging system further comprises a processor for controlling the medical imaging system and for controlling the adjustable focus of the catheter. The medical imaging system further comprises a memory containing machine executable instructions for execution by the processor. Execution of the instructions causes the processor to acquire medical image data by controlling the medical imaging system. Execution of the instructions further causes the processor to register a location of the distal end of the catheter in the medical image data. Execution of the instructions further causes the processor to generate focus control signals in accordance with the registered location at the distal end. Execution of the instructions further causes the processor to control the focus using the catheter interface in accordance with the focus control signals.

The medical imaging system may be one of a variety of different types of systems. For instance the medical imaging system may be a magnetic resonance imaging system. The medical imaging system may also be a computer tomography or CT system. The medical imaging system may also be a diagnostic ultrasound system. The form of the registration of the location may depend upon the type of medical image data acquired from a particular medical imaging system. In some embodiments the step of registering a location of the distal end of the catheter in the medical image data may comprise reconstructing a medical image from the medical image data and then registering the location in the medical image. Standard image recognition or registration techniques may then be used to register the location of the distal end of the catheter in the medical imaging data. This embodiment is particularly advantageous because the medical imaging data may be used to guide the heating of the target zone by the catheter. The catheter interface may supply power for the catheter to function. Additionally the processor may be able to send control signals or control the catheter interface such that the adjustable focus is controlled by the processor.

As an example a catheter where at least one array of capacitive micromachined ultrasound transducers forms a ring around the shaft may be inserted into a subject. Medical image data may then be used to determine which of the capacitive micromachined ultrasound transducers are energized to perform a particular therapy.

In another embodiment the medical imaging system is a magnetic resonance imaging system.

In another embodiment the medical imaging system is a computed tomography system.

In another embodiment the medical imaging system is a diagnostic ultrasound system.

In another embodiment the instructions further cause the processor to register a target zone of a subject in accordance with the medical image data. The step of registering the target zone may comprise reconstructing one or more medical images from the medical image data. The target zone may be registered using known image registration techniques. For instance certain anatomical landmarks may be found in the medical image or medical image data or a model such as a deformable-shaped model may be fit to the medical image data or the medical image. The instructions further cause the processor to generate focus control signals to control the focus such that the target zone is heated using the at least one array of capacitive micromachined ultrasound transducers. This embodiment is advantageous because a particular target zone is selected and targeted by the medical imaging system. In some embodiments a treatment plan or other planning data may be used to specify the target zone in advance.

In another embodiment execution of the instructions further causes the processor to acquire thermal imaging data using the medical imaging system. Thermal imaging data as used herein encompasses medical image data which may be used to measure or infer the temperature of different anatomical regions of a subject. The thermal imaging data may be the same or different from the medical image data. For some medical imaging modalities the thermal imaging data and the medical image data may be identical. In others the medical image data may comprise anatomical data and the thermal imaging data may comprise primarily data useful for constructing a thermal map. Execution of the instructions further causes the processor to reconstruct a thermal map using the thermal imaging data. A thermal map as used herein encompasses location specific temperature or description of temperature. For instance a thermal map may be superimposed on another medical image to indicate the temperature of different anatomical regions. The focus control signals are generated in accordance with the thermal map. That is to say the focus control signals may be generated using the thermal imaging data and/or the medical image data. The focus control signals can therefore be used to take into account internal anatomy of the subject and/or the temperature of different anatomical regions. This for instance may be used to ensure that a certain anatomical region is heated above a certain threshold temperature and is held there for a predetermined amount of time. This may be useful for inducing necrosis of cells or it may also be useful for activating thermally sensitive drugs or contrast agents.

The temperature of a subject may be measured using magnetic resonance thermometry. In magnetic resonance thermometry, magnetic resonance thermometry data is acquired. Magnetic resonance thermometry data is, in some embodiments, thermal imaging data. Magnetic resonance thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

Computed tomography may also be used to determine the temperature of a subject and therefore be used to acquire thermal imaging data. Computed tomography may for instance be used to detect a change of the Hounsfield unit of a region. This may be correlated to temperature. For example, a heated region may be identified as a hypodense zones in the images. Bubbles induced by cavitation may also be detected using computed tomography.

Ultrasound may also be useful to determine temperature and acquire thermal imaging data. This may be accomplished in several ways. For instance ultrasound may be used to determine temperature by measuring: echo shifts due to changes in tissue thermal expansion and speed of sound, variations in the attenuation coefficient, and/or change in backscattered energy from tissue inhomogeneities.

In another aspect the invention also provides for a computer program product comprising machine executable instructions for execution by a processor of a medical imaging system for acquiring medical image data from an imaging zone. The medical imaging system comprises a catheter interface for connecting to the connector of a catheter according to an embodiment of the invention. Execution of the instructions causes the processor to acquire medical image data in the medical imaging system. Execution of the instructions further causes the processor to register a location of the distal end of the catheter in the medical image data. Execution of the instructions further causes the processor to generate focus control signals in accordance with the registered location of the distal end. Execution of the instructions further causes the processor to control the focus using the catheter interface in accordance with the focus control signals. Execution of the instructions further causes the processor to control the focus using the catheter interface in accordance with the focus control signals.

The computer program product also provides for a computer-readable storage medium. The computer program product or machine executable instructions may be stored on a computer-readable storage medium.

In another aspect the invention provides for a method of operating a medical imaging system for acquiring medical image data from an imaging zone. The medical imaging system comprises a catheter interface for connecting to the connector of a catheter according to an embodiment of the invention. The method comprises the step of acquiring medical image data using the medical imaging system. The method further comprises the step of registering a location of the distal end of the catheter in the medical image data. The method further comprises the step of generating focus control signals in accordance with the registered location of the distal end. The method further comprises the step of controlling the focus using the catheter interface in accordance with the focus control signals.

Likewise the method may be implemented by a computer system or a processor. The invention therefore also provides for a computer-implemented method.

BRIEF DESCRIPTION OF THE DRAWINGS

In the following preferred embodiments of the invention will be described, by way of example only, and with reference to the drawings in which:

FIGS. 5a to 5b show a catheter according to a further embodiment of the invention, FIG. 10 shows a catheter according to a further embodiment of the invention, FIG. 11 shows a catheter according to a further embodiment of the invention.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
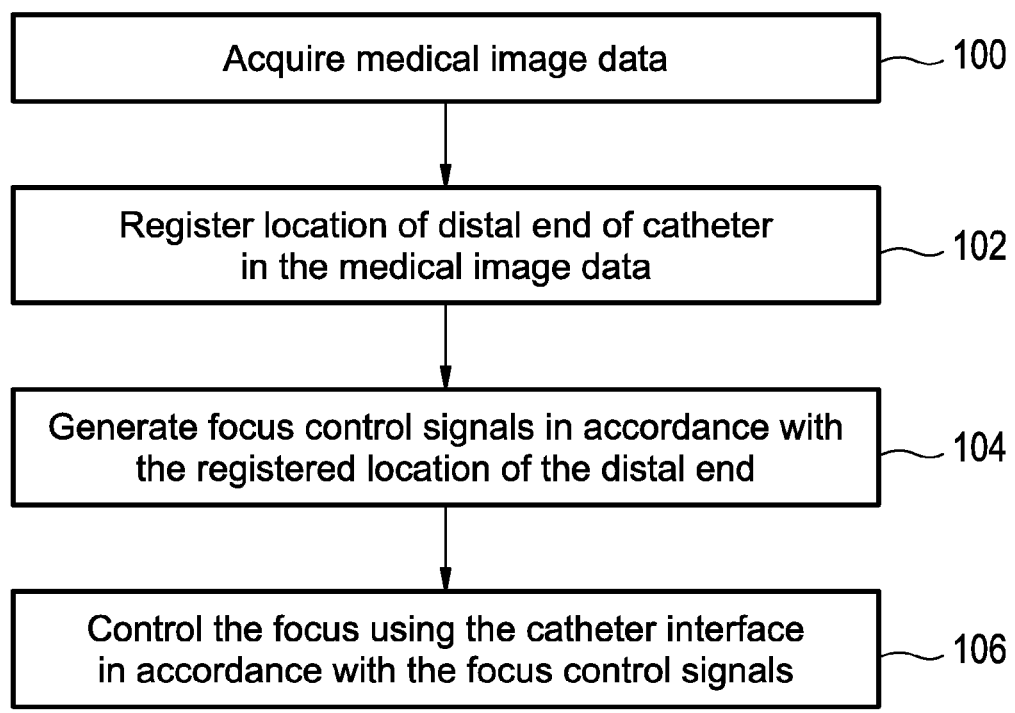
FIG. 1 shows a flow chart which illustrates a method according to an embodiment of the invention.

FIG. 1 shows a flow diagram which illustrates a method according to an embodiment of the invention. In step 100 medical image data is acquired. In step 102 a location of a distal end of the catheter is registered in the medical image data. The distal end of the catheter may be recognized using image recognition techniques. For instance a portion of the catheter may be identified outside of the subject and the catheter may have a particular appearance in the particular medical imaging modality. For instance the catheter may be made of a material which has particularly large or low contrast in a particular imaging modality. The catheter may also have a shape or contain a region which is easily identifiable in the medical image data. Step 102 may also comprise the steps of reconstructing the medical image data into one or more medical images. In this case the location would have been registered in the medical image.

In the case where image registration is not performed, identifying the location of the distal end using a marker or identifier easily recognized by the imaging modality of the medical imaging system may be used. For instance the distal end may have an ultrasound beacon for identification if the imaging modality is ultrasound. For magnetic resonance imaging a resonant RF coil that is excited during the acquisition of magnetic resonance data may be used to identify the location of the distal end.

Next in step 104 focus control signals are generated in accordance with the registered location of the distal end. Next in step 106 the focus is controlled using the catheter interface in accordance with the focus control signals. This may take several different forms. If there is a mechanical system for directly focusing the catheter interface the focus control signals may cause the interface to actuate that portion of the catheter which controls the mechanical aspect of the focus. If individual capacitive micromachined ultrasound transducers are controlled by the interface then the focus control signals may comprise instructions for controlling the power delivered to the micromachined ultrasound transducers. If the at least one array of capacitive micromachined ultrasound transducers are driven by an integrated circuit then the focus control signals may simply contain instructions which are delivered to the integrated circuit via a data bus.

Figure 2:
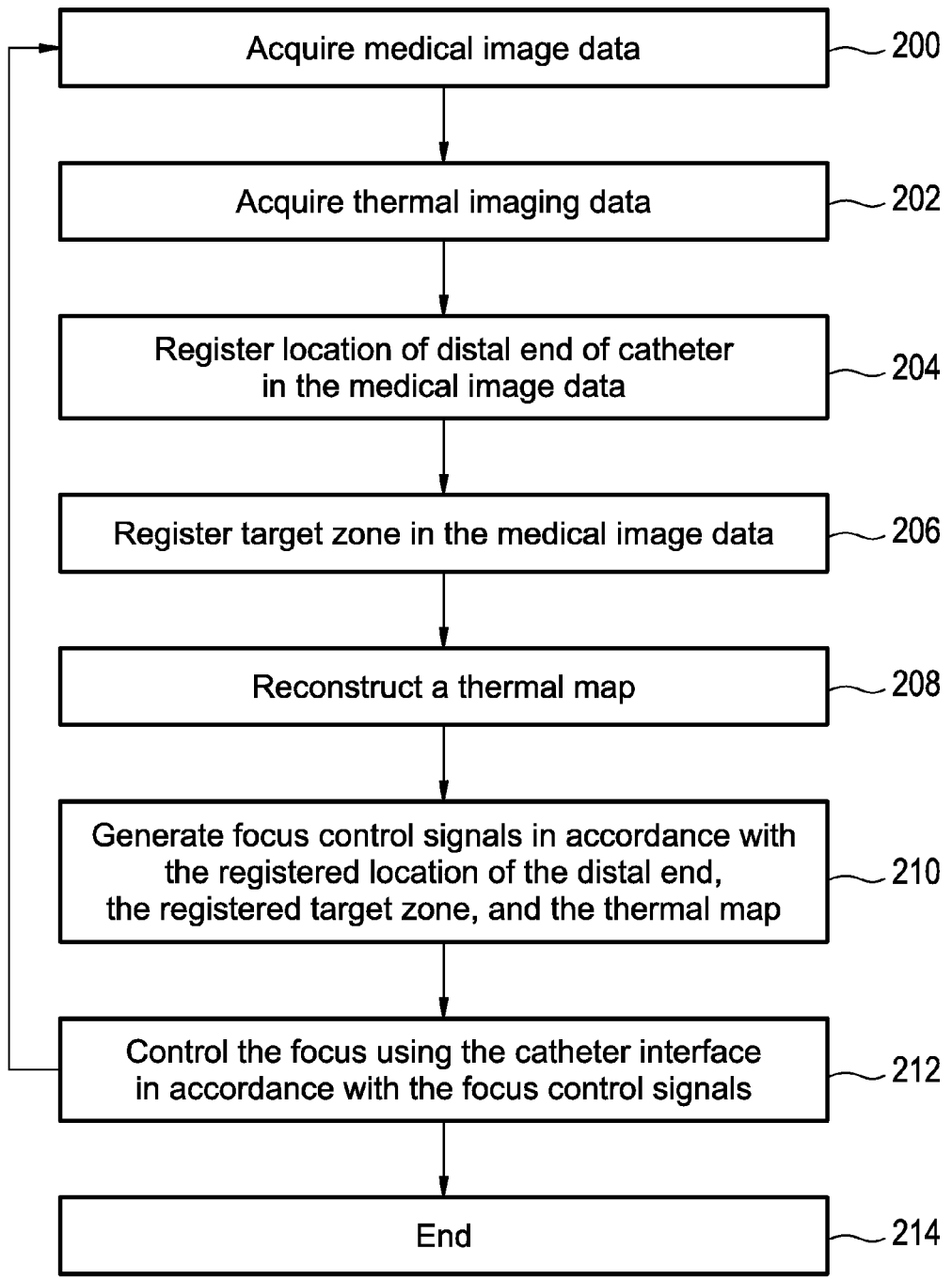
FIG. 2 shows a flow chart which illustrates a method according to a further embodiment of the invention.

FIG. 2 shows a flow diagram which illustrates a method according to a further embodiment of the invention. In step 200 medical image data is acquired. In step 202 thermal imaging data is acquired. In some embodiments the medical image data and the thermal imaging data may be acquired at the same time or reconstructed from the same data. In step 206 allocation of the distal end of the catheter is registered in the medical image data. As previously discussed step 204 may also involve the act of reconstructing a medical image from the medical image data. In step 206 a target zone is registered in the medical image data. The target zone may be in some embodiments identified initially in a treatment plan or in planning data which is delivered to the medical imaging system. In step 208 a thermal map is reconstructed from the thermal imaging data. In step 210 focus control signals are generated in accordance with the registered location of the distal end, registered target zone, and the thermal map. In step 212 the focus is controlled using the catheter interface in accordance with the focus control signals. In the flowchart there is an arrow going from block 212 back to block 200. This indicates that these steps of the method may be performed repeatedly. For instance during the course of heating the target zone the subject may move or there may be a need for monitoring the temperature of the target zone and portions of the subject surrounding the target zone. The thermal maps measured during heating can be used for closed loop feedback of the treatment to ensure a predetermined amount of heating that does not exceed a predetermined threshold level of heating. Although all steps from steps 200-212 are shown as being in a loop, in some embodiments not all of these steps may be performed every loop. For instance if the subject is not moving it may be desired only to repeatedly acquire thermal imaging data during each loop. Likewise, if the temperature of the target zone is not changing rapidly but however there is internal motion or external motion of the subject, it may be beneficial to acquire the medical imaging data more often than the thermal imaging data. Finally, after the heating of the target zone has finished, the method ends in step 214.

Figure 3:
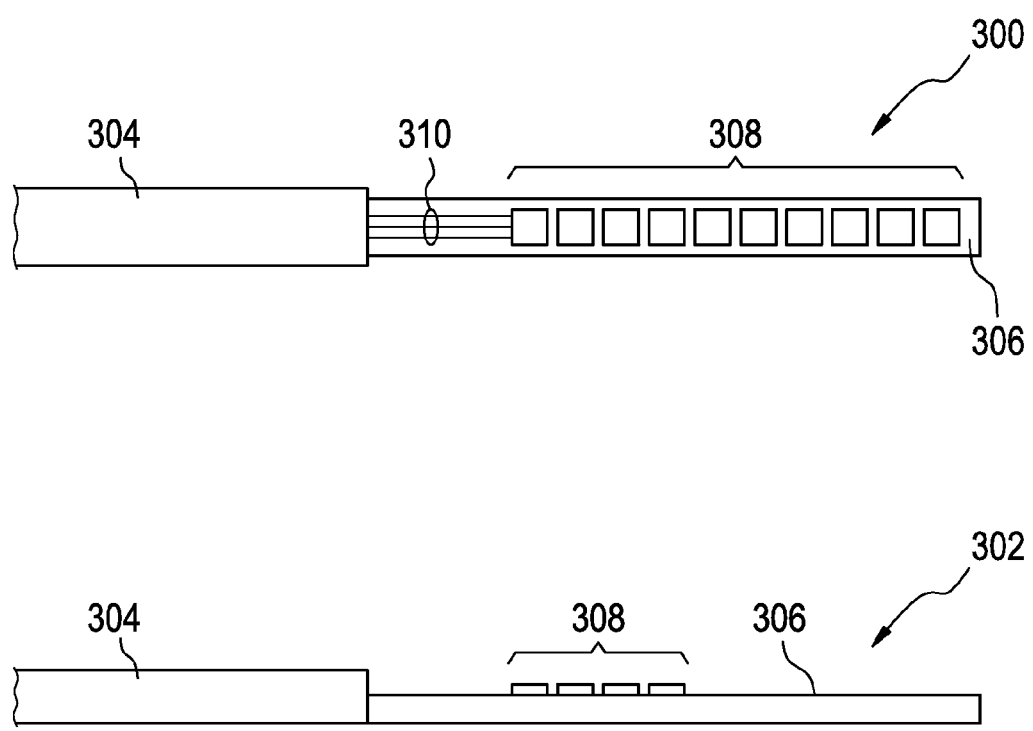
FIG. 3 shows a catheter according to an embodiment of the invention, FIG. 4 compares several types of capacitive micromachined ultrasound transducer arrays to a convention piezoelectric transducer.

FIG. 3 shows a top view 300 and a side view 302 of a catheter 304 according to an embodiment of the invention. In the example shown in FIG. 3 only the distal end of the catheter is shown. In this design there is a flat surface 306 with arrays 310 of capacitive micromachined ultrasound transducers. In this example there are ten arrays 308. The bottom view 302 does not show all of the arrays 308 shown in the top view 300. In this embodiment each of the arrays 308 is connected to an individual electrical cable 310.

Figure 4:
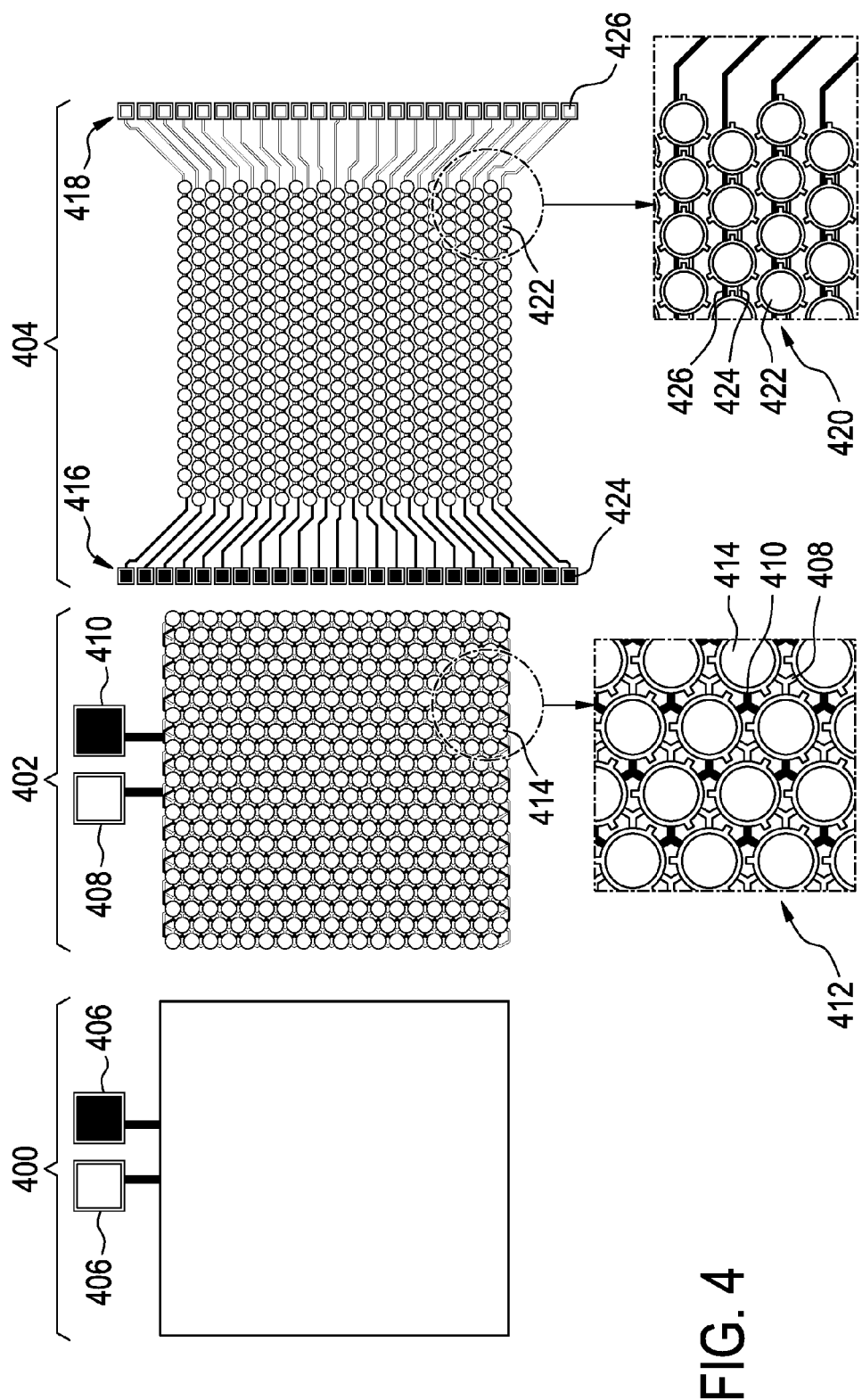

In FIG. 4 a conventional piezoelectric element 400 is shown. Next to the piezoelectric element 400 are two arrays 402, 404 of capacitive micromachined ultrasound transducers. The piezoelectric element 400 has two electrical connections 406 for driving the element 400.

The capacitive micromachined ultrasound transducer array 402 has first 408 and second 410 electrical connections. Array 402 is wired so that it functions as a single transducer element in the way that the piezoelectric element 400 does. This demonstrates how an array 402 may be used as a replacement for an entire piezoelectric element 400. Drawing 412 shows a blowup of array 402. The individual capacitive micromachined ultrasound transducers 414 can be seen. It can be seen that each of the transducers 414 is connected to the first 408 and second 410 electrical connections. The array 404 of capacitive micromachined ultrasound transducers is arranged as linear arrays. There is a set of first 416 and second 418 electrical connections for each row of transducers. Drawing 420 is a blowup detail of the array 404. An individual capacitive micromachined ultrasound transducer 422 can be shown as being connected to a first 424 and second 426 electrical connection. The connections 424 and 426 are chosen from the first 416 and second 418 sets of electrical connections.

In addition to wiring the capacitive micromachined ultrasound transducers in large block arrays or in linear arrays the individual micromachined ultrasound transducers may also be individually driven by their own source.

FIGS. 5a and 5b illustrate one method of cooling capacitive micromachined ultrasound transducers. In FIG. 5a there is a substrate 500 with arrays of capacitive micromachined ultrasound transducers built into it. This is formed on substrate 502. Substrate 502 may for instance be a silicon substrate. Beneath this the arrow 504 indicates channels for fluid flow for cooling the substrate with the arrays 500. There are fins 506 which facilitate the transfer of thermal energy from the substrates 500 and 502 to the cooling fluid. The frequency generated by a capacitive micromachined ultrasound transducer is independent of its thickness, this is in contrast with a piezoelectric transducer. Thus very low frequency capacitive micromachined ultrasound transducers may be very thin in comparison with a comparable piezoelectric crystal. The distance 510 indicates the combined thickness of the capacitive micromachined ultrasound transducer 500 and the substrate 502.

FIG. 5b shows an altered way of manufacturing such an embodiment. In FIG. 5b there is a substrate 512 of arrays of capacitive micromachined ultrasound transducers. The substrate with the arrays 512 is mounted on a substrate 514. The substrate 514 may also be made of silicon. Inside the substrate 514 are micro-channels 516 that have been micromachined into the substrate. The arrow 518 indicates the direction of fluid flow through the micro-channels 516.

Figure 6A:
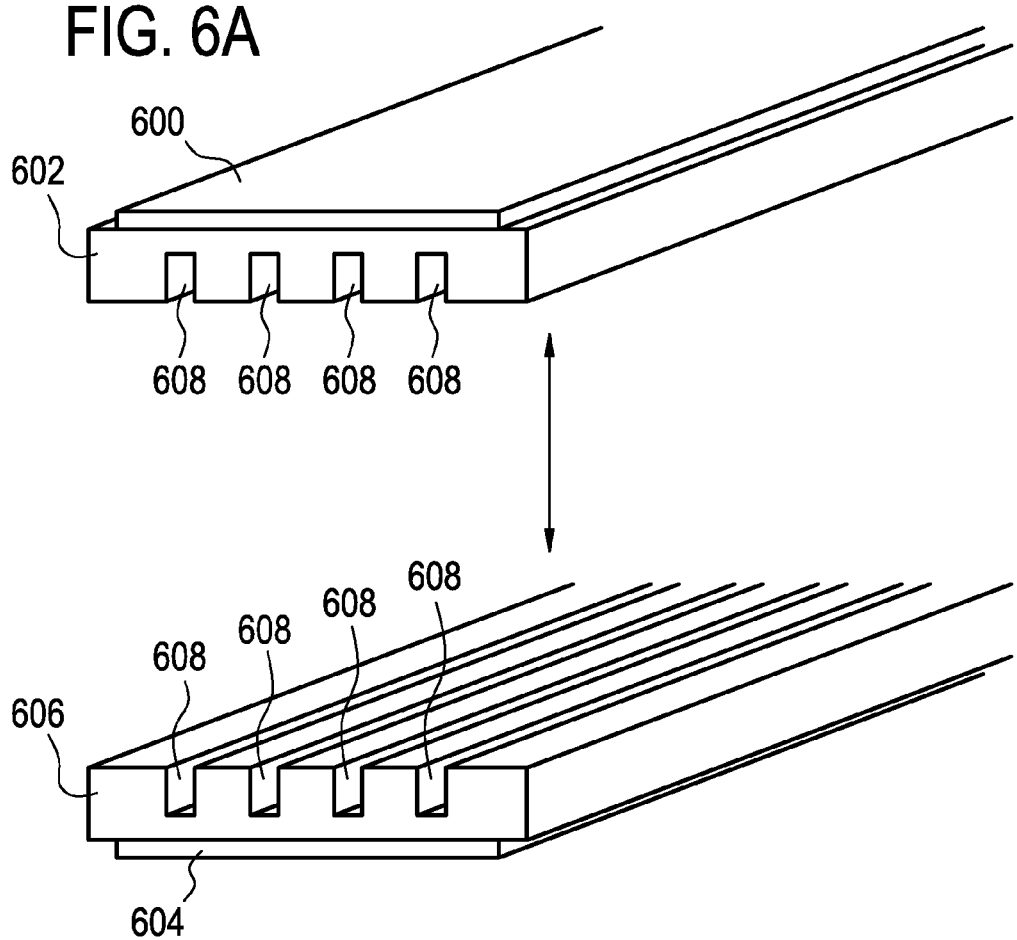
FIGS. 6a to 6b show a catheter according to a further embodiment of the invention.
Figure 6B:
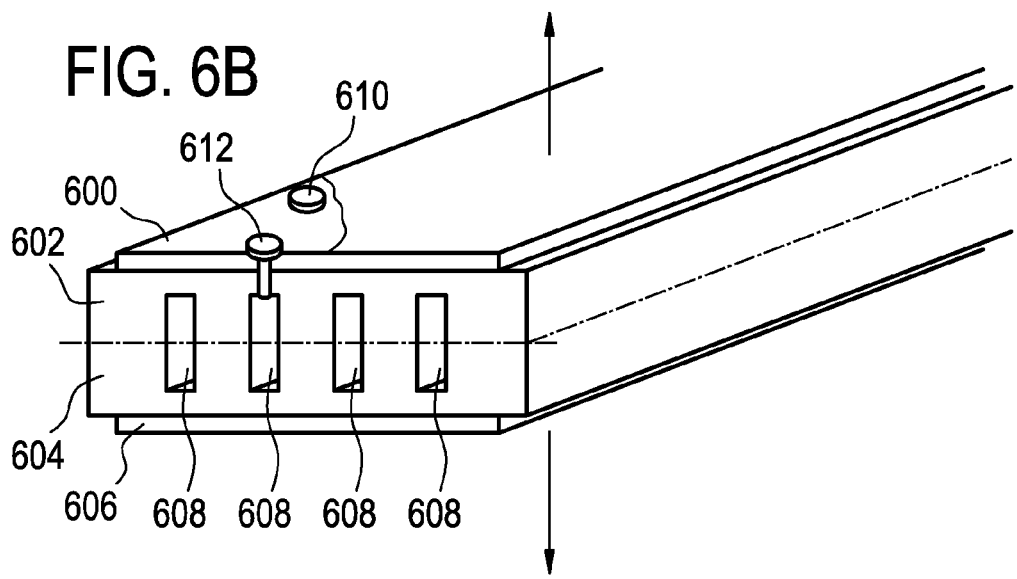

FIGS. 6a and b show a two-sided distal end of a catheter according to an embodiment of the invention. FIG. 6a illustrates the construction and FIG. 6b shows the assembled piece. In this example there is a top half which has a first substrate 600 with arrays of capacitive micromachined ultrasound transducers attached to another first substrate 602. The first substrate 602 may also be out of silicon. There is a second substrate 604 with arrays of capacitive micromachined ultrasound transducers on a second substrate 606. The second substrate 606 may be out of silicon. In the substrates 602 and 606 there are channels 608 which have been cut. They for instance may be cut using standard silicon micromachining such as chemical or plasma etching. The substrate 602 and 606 may be glued together using suitable adhesive such as BCB. In FIG. 6b the two halves have been assembled together. Additionally shown in FIG. 6b is a temperature sensor 610 shown on the surface of substrate 600 and a flow or pressure sensor 612 which measures the flow or pressure in one of the channels 608.

Figure 7:
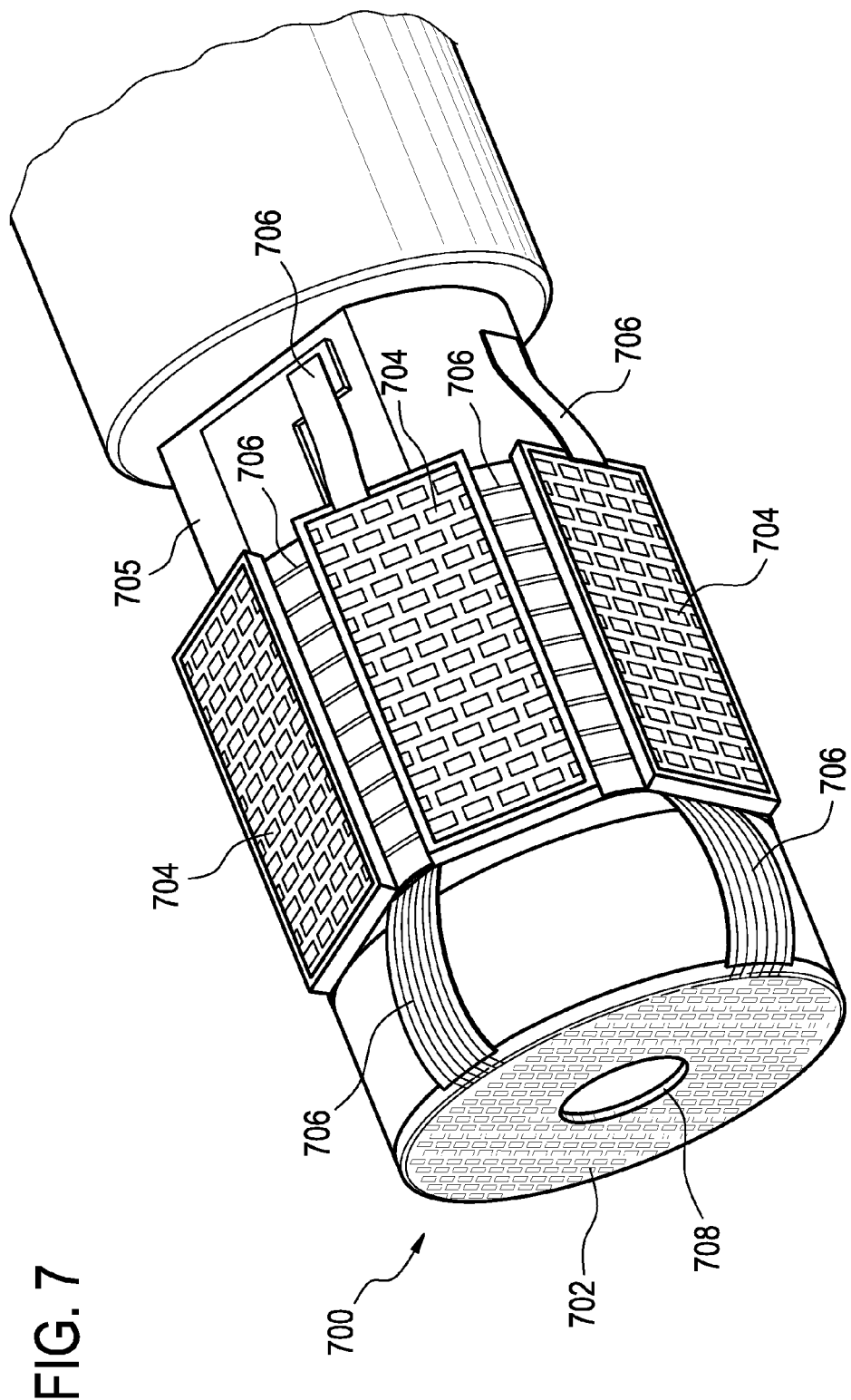
FIG. 7 shows a catheter according to a further embodiment of the invention.

FIG. 7 shows a distal end 700 of a catheter according to an embodiment of the invention. In this embodiment there is a forward-looking ring array 702. There is an array of capacitive micromachined ultrasound transducers surrounding a hole 708. Behind the ring array 702 are panels of sideways-looking arrays 704. The arrays 704 form a ring around the shaft of the catheter. Shown in this FIG. are various electrical connections 706. The forward-looking ring array 702 may be used for such things as providing three dimensional imaging. The sideways-looking arrays 704 may be used for ultrasound ablation and monitoring. The individual capacitive micromachined ultrasound transducers can be used for beam steering during ultrasound ablation. Benefits of this embodiment may include that there is no or minimal need for mechanically rotating the catheter. The hole 708 can be used for additional instruments or for water irrigation. The embodiment shown in FIG. 7 can focus in multiple directions so for such things as ablating a prostrate the entire 360 degrees around the probe may be performed simultaneously. This would result in less treatment time and thus also reduce costs.

Figure 8:
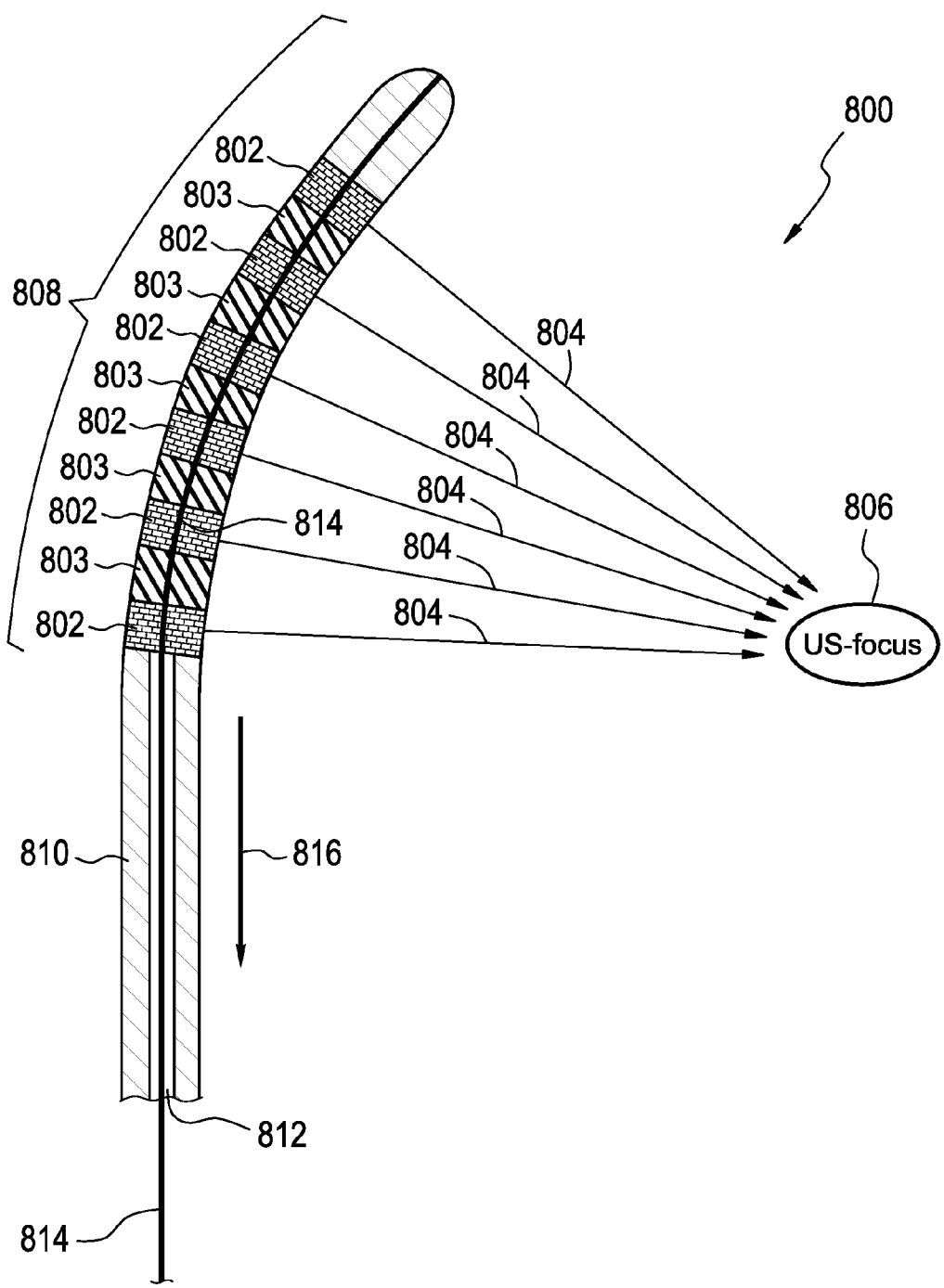
FIG. 8 shows a catheter according to a further embodiment of the invention.

FIG. 8 shows a catheter 800 where the focus is adjusted mechanically. The catheter has arrays 802 of capacitive micromachined ultrasound transducers. The arrays in this embodiment may be flexible or they may be rigid. Shown is a flexible element 803 between each of the arrays 802. The lines 804 trace the general path of the ultrasound generated by the arrays 802. The ultrasound 804 concentrates in a target zone 806. All of the arrays 802 are located on the distal end 808 of the shaft 810 of the catheter 800. There is a curvature at the distal end 808. This causes the collection of arrays 802 to focus their ultrasound in the target zone 806. Such an arrangement could be adjusted mechanically. For instance located within the catheter could be a tube 812 which is mounted rigidly or semi-rigidly to the shaft 810. Within the tube 812 could be a cable 814. The cable could extend up from the tube 812 through the distal end 808 of the catheter 800. The distal end 808 could for instance have a springy material or be pre-stressed. This may cause a natural curvature of the distal end 808. When the cable is pulled or moved in the direction 818 this causes the cable 814 to shorten which may cause the distal end 808 to straighten. This would change the focus of the catheter 800. The cable 814 could also be used to manipulate a linkage. The mechanical adjustment of this catheter may be used, in some embodiments, to actively steer or guide the catheter. In other words the mechanical adjustment for the focus may be used to mechanically adjust the position of the distal end.

Figure 9:
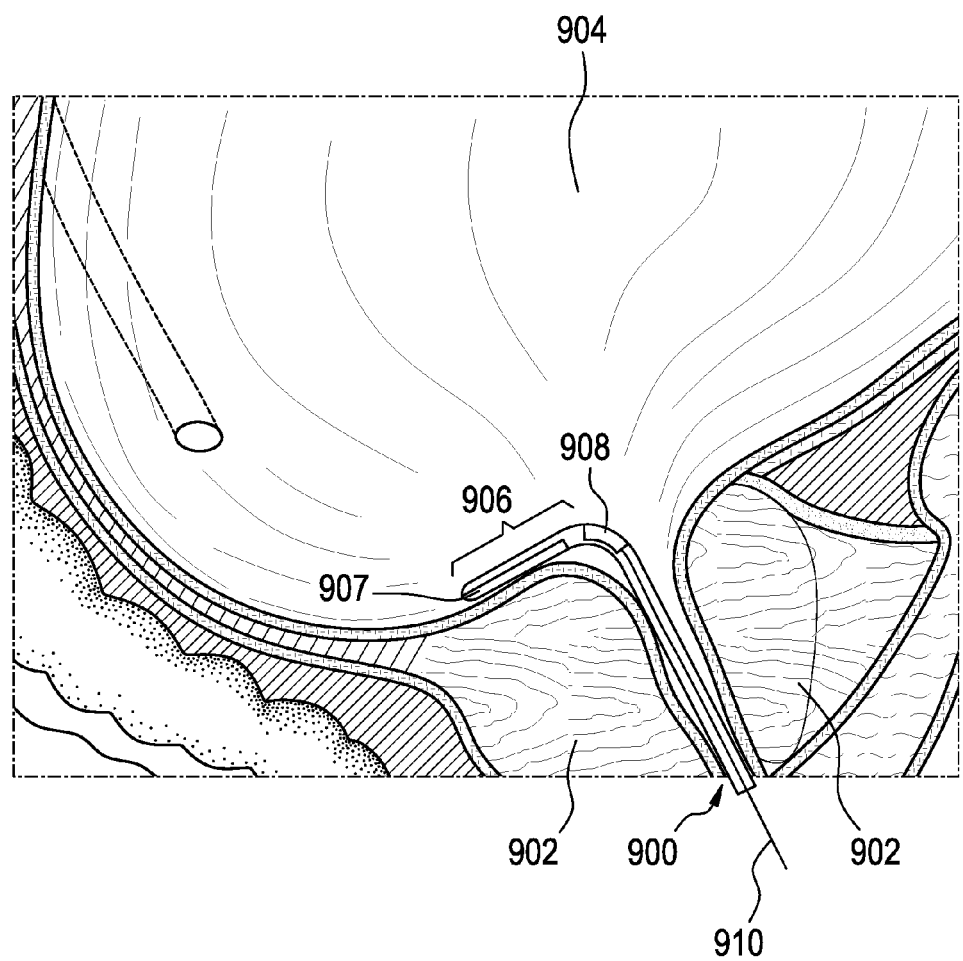
FIG. 9 shows a catheter according to a further embodiment of the invention.

FIG. 9 shows a catheter 900 according to an embodiment of the invention being used to treat a prostrate 902. The catheter 900 has been inserted through the urethra and into the bladder 904. In this embodiment the distal end 906 of the catheter 900 has an array 907 of capacitive micromachined ultrasound transducers. There is a mechanical actuator 908 which flexes the distal end 906. There is a cable 910 for controlling the mechanical actuator 908. The embodiment shown in FIG. 9 can be shown as being advantageous because the catheter 900 may be inserted into the bladder and then the mechanical actuator 908 is used to position the array of capacitive micromachined ultrasound transducers 907 such that the prostrate 902 can be sonicated. A benefit of this embodiment is that the catheter 900 may enable sonication of the prostate from the bladder. The added mechanical freedom in the bladder may aid in positioning the catheter effectively and reduce the risk of damaging healthy tissue.

FIG. 10 shows a further embodiment of a catheter 1000 according to an embodiment of the invention. The catheter 1000 has a shaft 1002 with a distal end 1004 and a proximal end 1006. At the distal end 1004 there are multiple arrays 1008 of capacitive micromachined ultrasound transducers. Each of the arrays 1008 has its own electrical connection 1010 to a connector 1012 at the proximal end 1006. When supplied with electrical power the arrays 1008 deposit ultrasonic energy in a target zone 1014 which is adjacent to or to the side of the shaft 1002.

FIG. 11 shows a further embodiment of a catheter 1100 according to an embodiment of the invention. The embodiment shown in FIG. 11 is very similar to that shown in FIG. 10 but several features have been added. In this embodiment the individual arrays 1008 are connected to an integrated circuit 1102 instead of being connected directly to the connector 1012. The integrated circuit 1102 is connected to the connector 1012 by data bus 1010' which functions as supplying both power and a data connection. Via the data bus 1010' the integrated circuit 1102 receives instructions for how to drive the individual arrays 1008. The integrated circuit 1102 is also shown as being connected to a pressure or flow sensor 1104 at the tip of the proximal end 1004. The integrated circuit 1102 is also shown as being connected to a temperature sensor 1106 which is mounted amongst the arrays 1008. Depending upon the embodiment the arrays 1008 and the integrated circuit 1102 can be used for ablation and/or for performing diagnostic ultrasound. In some embodiments some of the arrays 1008 may be used for performing ablation and some may be used for performing diagnostic ultrasound at the same time. At the connector 1012 is also a fluid cooling inlet 1108. The fluid cooling inlet 1108 is connected to a tube 1110 which is adapted for carrying cooling fluid to the proximal end 1004 for cooling it. At the tip of the proximal end 1004 is an outlet 1112. The proximal end 1004 is closed off with a seal 1114 so that cooling water or cooling fluid which comes in the tube 2010 is forced out through the outlet 1112. In other embodiments there may be a return tube and a fluid cooling outlet at the connector 1012.

Figure 12:
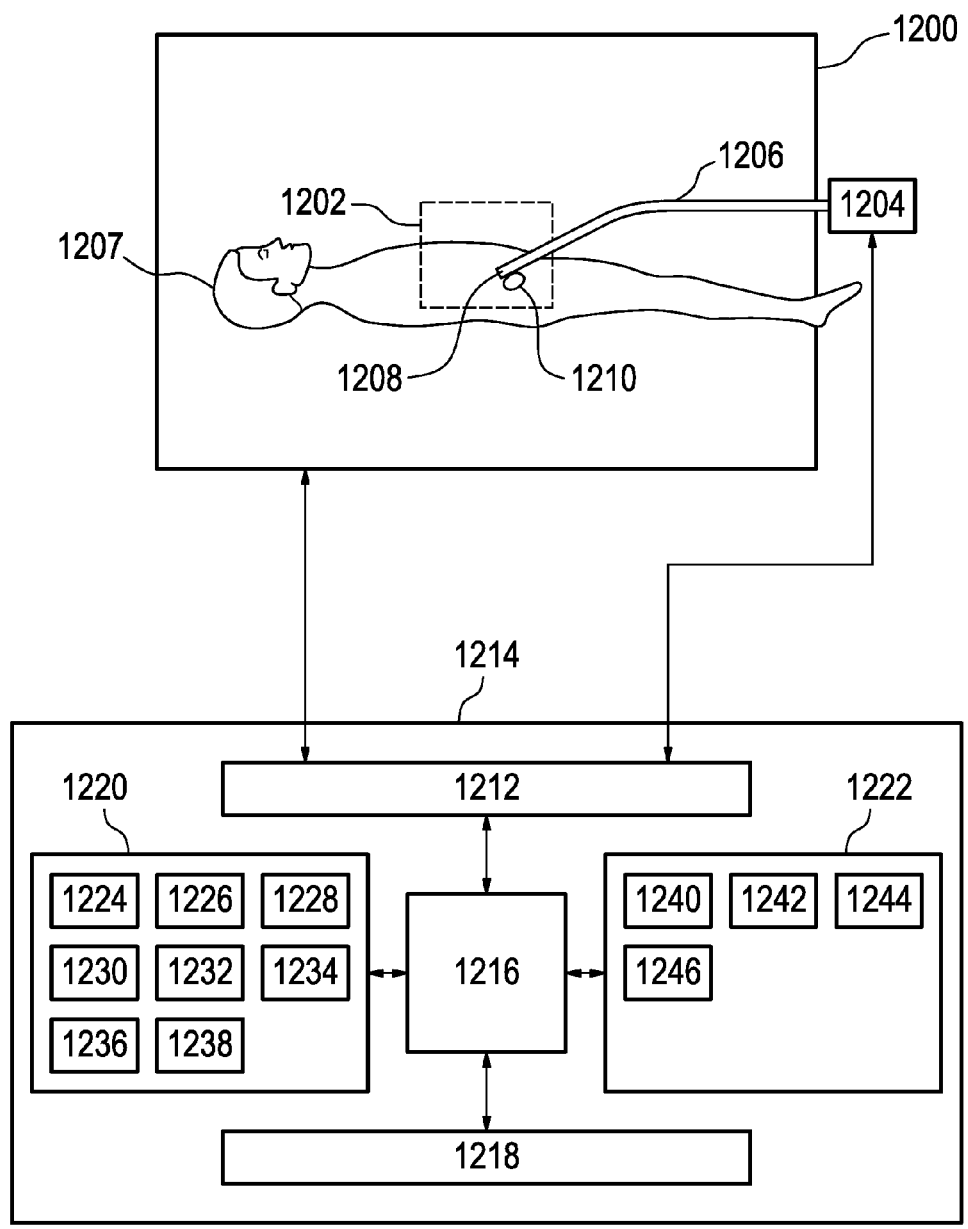
FIG. 12 illustrates a medical imaging system according to an embodiment of the invention.

FIG. 12 shows an embodiment of a medical imaging system 1200 according to an embodiment of the invention. The medical imaging system in this FIG. may be representative of many different types of medical imaging systems. For instance the medical imaging system may be a magnetic resonance imaging system, a computer tomography system, or a diagnostic ultrasound system. The medical imaging system 1200 is adapted for performing medical imaging in a medical imaging zone 1202. The medical imaging system 1200 also comprises a catheter interface 1204. Shown in the FIG. a catheter 1206 is connected via its connector to the catheter interface 1204. The catheter 1206 has been inserted into a subject 1207. The distal end 1208 is within the imaging zone 1202. A target zone 1210 which has been heated by the catheter 1206 is also shown within the imaging zone 1202. The medical imaging system 1200 and the catheter interface 1204 are both shown as being connected to a hardware interface 1212 of a computer system 1214. The computer system further comprises a processor 1216 for executing machine executable instructions. The processor is shown as being connected to the hardware interface 1212 and a user interface 1218. The hardware interface 1212 allows the processor 1216 to control the functionality of the medical imaging system 1200 and the catheter interface 1204. The processor 1216 is also shown as being connected to computer storage 1220 and computer memory 1222.

The computer storage 1220 is shown as containing a treatment plan 1224. The treatment plan may contain detailed instructions for treating the target zone 1220. The treatment plan may also contain anatomical landmarks which are later used in registering the location of the target zone 1210 and/or the distal end 1208. The computer storage 1220 is further shown as containing medical image data 1226 acquired from the imaging zone 1202. The computer storage 1220 is further shown as containing a medical image 1228 which has been reconstructed from the medical image data 1226. The computer storage 1220 is further shown as containing focus control signals 1230. The focus control signals 1230 contain signals the processor 1216 can use for controlling the catheter 1206 via the catheter interface 1204. Also within the computer storage 1220 are the location of the distal end 1232 and the location of the target zone 1234. Both of these locations 1232, 1234 have been determined by registering the medical image 1228. The computer storage 1220 is further shown as containing a thermal map 1238. The thermal map 1238 was reconstructed from the thermal imaging data 1236 which is also stored in the computer storage 1220.

The computer memory 1222 is shown as containing machine executable instructions for operating the medical imaging system 1200. The instructions contained in the computer memory 1222 may also be stored in the computer storage 1220. The computer memory 1222 is shown as containing a control module 1240. The control module 1240 contains machine executable instructions for controlling the function and operation of the medical imaging system 1200. The computer memory 1222 is further shown as containing an image reconstruction module 1242. The image reconstruction module 1242 is an optional module which may be used for reconstructing the medical image 1228 from the medical image data 1226. The computer memory 1222 is further shown as containing a thermal mapping module 1244. The thermal mapping module 1244 contains machine executable instructions for reconstructing a thermal map 1238 from the thermal imaging data 1236. The computer memory 1222 is shown as further containing a focus control signal generation module 1246. The focus control signal generation module 1246 is used for generating the focus control signals 1230. The focus control signals may use the treatment plan 1224, location of the distal end 1232, the location of the target zone 1234, the thermal map, or combinations thereof for generating the focus control signals 1230.

In using such a medical imaging system 1200 a physician may insert the catheter 1206 into the subject 1207. The subject 1207 is then placed such that the target zone 1210 is within the imaging zone 1202. The imaging system 1200 is then able to identify the location of the distal end 1208 and the target zone 1210. As the focus of the catheter 1206 is adjustable the processor 1216 is able to send commands to the catheter interface 1204 such that the target zone 1210 is heated by the catheter 1206. The target zone is controllably heated by the catheter 1206 and is automatically controlled by the computer system 1214.

Figure 13:
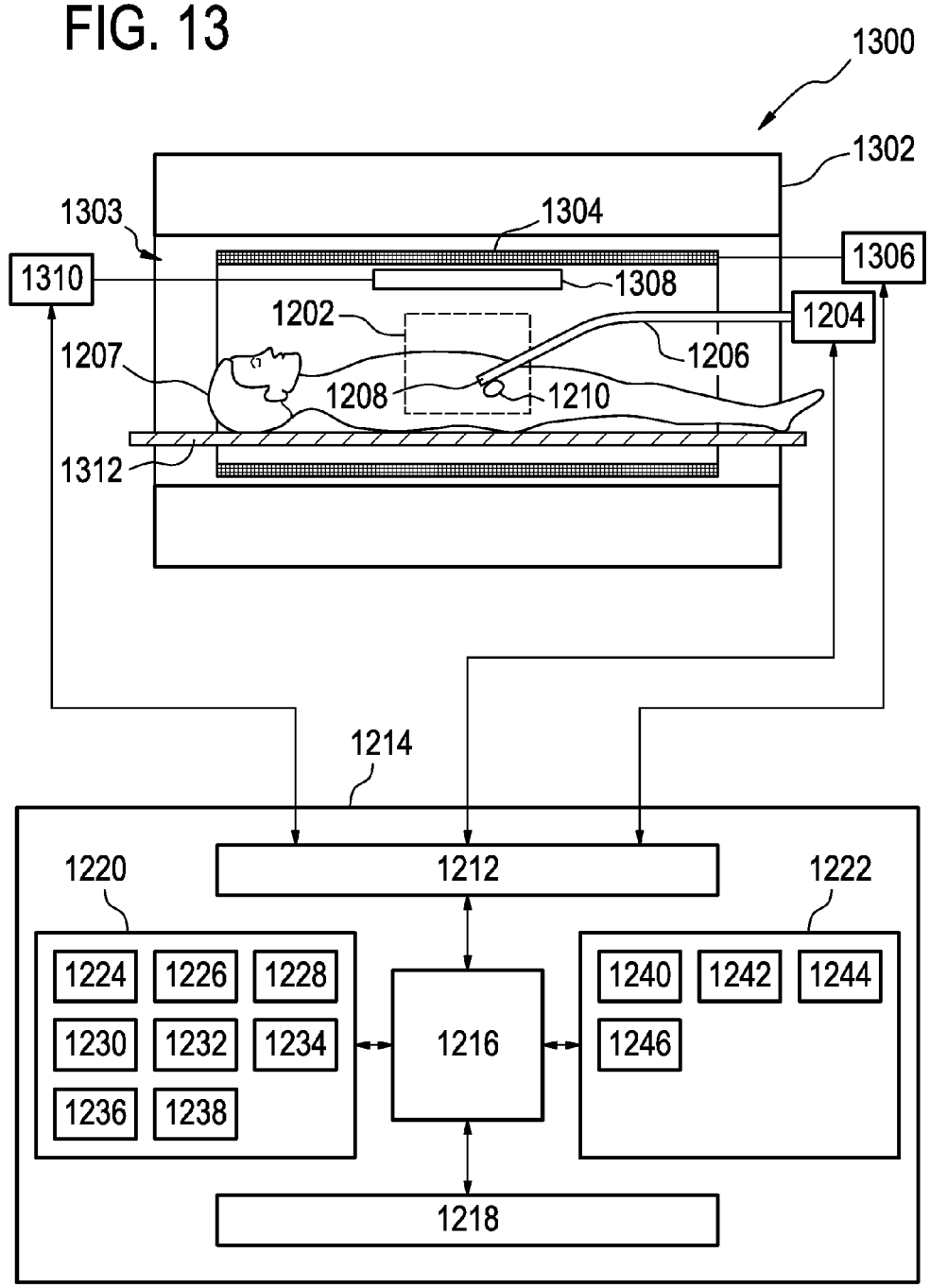
FIG. 13 illustrates a medical imaging system according to a further embodiment of the invention.

FIG. 13 shows a further embodiment of an imaging system according to an embodiment of the invention. The imaging system is a magnetic resonance imaging system 1300. The magnetic resonance imaging system comprises a magnet 1302. The magnet 1302 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

Within the bore of the magnet 1303 there is a magnetic field gradient coil 1304 which is supplied current by a magnetic field gradient coil power supply 1306. The magnetic field gradient coil 1304 is used to spatially encode magnetic spins within an imaging zone of the magnet during the acquisition of magnetic resonance data. The magnetic field gradient coil 1304 is intended to be representative. Typically magnetic field gradient coils contain three separate sets of coils for spatially encoding in three orthogonal spatial directions. The current supplied to the magnetic field coil 1304 is controlled as a function of time and may be ramped or pulsed.

Within the bore of the magnet 1303 is an imaging zone 1202 where the magnetic field is uniform enough for performing magnetic resonance imaging. Adjacent to the imaging zone 1202 is an antenna 1308. The antenna 1308 is connected to transceiver 1310. The radio frequency antenna 1308 is for manipulating the orientations of magnetic spins within the imaging zone 1202 and for receiving radio transmissions from spins also within the imaging zone. The radio frequency antenna may contain multiple coil elements. The radio frequency antenna may also be referred to as a channel. The radio frequency coil is connected to a radio frequency transceiver 1310. The radio frequency coil 1308 and radio frequency transceiver 1310 may be replaced by separate transmit and receive coils and a separate transmitter and receiver. The radio frequency antenna is intended to also represent a dedicated transmit antenna and a dedicated receive antenna. Likewise the transceiver 1310 may also represent a separate transmitter and receivers.

The subject 1207 is seen as reposing on subject support 1312. As in FIG. 12 the catheter 1206 has been inserted into the subject 1207. The transceiver 1310, the gradient coil power supply 1306 and the catheter interface 1204 are all shown as being connected to the hardware interface 1212 of computer system 1214. The computer system 1214 in FIG. 13 is equivalent to the computer system 1214 in FIG. 12. The various software components stored in computer memory 1222 and the contents of the computer storage 1220 are equivalent in the two Figs. The medical imaging data 1226 in the embodiment shown in FIG. 13 is magnetic resonance data. The thermal imaging data 1236 is magnetic resonance thermometry data.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

300 top view
302 side view
304 catheter
306 flat surface
308 array of capacitive micromachined ultrasound transducers
310 cable
400 piezo element
402 array of capacitive micromachined ultrasound transducers
404 array of capacitive micromachined ultrasound transducers
406 electrical connections
408 first electrical connection 410 second electrical connection
412 blowup view of array 402
414 capacitive micromachined ultrasound transducer
416 set of first electrical connections
418 set of second electrical connections
420 blowup view of array 404
422 capacitive micromachined ultrasound transducer
424 first electrical connection
426 second electrical connection
500 substrate with arrays of capacitive micromachined ultrasound transducers
502 substrate
504 channels for fluid flow
506 fins
508 direction of generated ultrasound beam
510 thickness
512 substrate with arrays of capacitive micromachined ultrasound transducers
514 substrate
516 micromachined micro-channels
518 fluid flow
600 first substrate with arrays of capacitive micromachined ultrasound transducers
602 first substrate
604 second substrate with arrays of capacitive micromachined ultrasound transducers
606 second substrate
608 channel
610 temperature sensor
612 flow or pressure sensor
700 distal end of catheter
702 forward looking ring array
704 sideward looking array
705 shaft
706 electrical connection
708 hole
800 catheter
802 array of capacitive micromachined ultrasound transducers
803 flexible element
804 path of ultrasound
806 target zone
808 distal end
810 shaft
812 tube
814 cable
816 direction of cable travel
900 catheter
902 prostate
904 bladder
906 distal end
907 array of capacitive micromachined ultrasound transducers
908 mechanical actuator
910 cable
1000 catheter
1002 shaft
1004 distal end
1006 proximal end
1008 array of capacitive micromachined ultrasound transducers
1010 electrical connections
1010' data bus and power supply
1012 connector
1014 target zone
1100 catheter
1102 processor
1104 flow or pressure sensor
1106 temperature sensor
1108 fluid cooling inlet
1110 tube
1112 outlet
1114 seal
1200 medical imaging system
1202 imaging zone
1204 catheter interface
1206 catheter
1207 subject
1208 distal end
1210 target zone
1212 hardware interface
1214 computer system
1216 processor
1218 user interface
1220 computer storage
1222 computer memory
1224 treatment plan
1226 medical image data
1228 medical image
1230 focus control signals
1232 location of distal end
1234 location of target zone
1236 thermal imaging data
1238 thermal map
1240 control module
1242 image reconstruction module
1244 thermal mapping module
1246 focus control signal generation module
1300 magnetic resonance imaging system
1302 magnet
1303 bore of magnet
1304 magnetic field gradient coil
1306 magnetic field gradient coil power supply
1308 antenna
1310 transceiver
1312 subject support

The invention claimed is:

1. A catheter comprising:
a shaft with distal and proximal ends, wherein the distal end comprises a transducer module with at least one array of capacitive micromachined ultrasound transducers, the at least one array of capacitive micromachined ultrasound transducers having an adjustable focus for controllably heating a target zone, the distal end further comprising at least one integrated circuit wherein the at least one array of micromachined ultrasound transducers is connected to the integrated circuit; and
a connector disposed at the proximal end, and
a data bus connecting the at least one integrated circuit disposed at the distal end to the connector to supply focus control instructions from the connector to the at least one integrated circuit, the at least one array of micromachined transducers not being connected to the connector,
wherein the transducer module is partly flexible.

2. The catheter as claimed in claim 1, wherein the at least one array of capacitive micromachined ultrasound transducers is disposed on a flexible substrate, wherein the at least one array of capacitive micromachined ultrasound transducers is flexible.

3. The catheter of claim 1, wherein the transducer module comprises at least two arrays of capacitive micromachined ultrasound transducers, and wherein the catheter further comprises a flexible element between the at least two arrays of capacitive micromachined ultrasound transducers.

4. The catheter of claim 1, wherein the transducer module includes at least one two-dimensional array of capacitive micromachined ultrasound transducers orientated such that a target zone is located adjacent a side of the catheter tip.

5. The catheter of claim 4, further including:
a plurality of two-dimensional arrays of capacitive micromachined ultrasound transducers disposed in a ring around the shaft such that the ultrasound signal can be focused on a target zone to any side of the tip without rotating the catheter by selecting among the plurality of two-dimensional arrays.

6. The catheter of claim 1, wherein the distal end comprises at least one integrated circuit for imaging and for powering the at least one array of capacitive micromachined ultrasound transducers and for providing electronic control of the adjustable focus based on the imaging.

7. The catheter of claim 1, wherein the connector comprises a fluid cooling inlet at the proximal end, and wherein the catheter is adapted for supplying the distal end with cooling fluid from the fluid cooling inlet.

8. The catheter of claim 7, wherein the array of capacitive micromachined ultrasound transducers is a two-dimensional array with a pressure sensor configured to measure cooling fluid pressure and a temperature sensor integrally formed in the two-dimensional array.

9. The catheter of claim 7, wherein the catheter further comprises a flow sensor integrated with the at least one array of capacitive micromachined ultrasound transducers.

10. The catheter of claim 7, wherein the catheter further comprises a pressure sensor arranged to measure cooling fluid pressure in the distal end, and a flow sensor arranged to measure cooling fluid flow.

11. The catheter of claim 1, further including:
an integrated circuit in the catheter configured to:
generate at least a temperature map of the target zone, based on signals from the array of capacitive micromachined ultrasound transducers, and
control and focus power ultrasonically delivered to the target zone by the at least one array of capacitive micromachined ultrasound transducers based on the temperature map.

12. The catheter of claim 11, wherein the integrated circuit is configured to control the array of capacitive micromachined ultrasound transducers to deliver non-ablation, extended hyperthermia for at least one of localized drug delivery and gene therapy.

13. The catheter of claim 1, wherein the array of capacitive micromachined ultrasound transducers is integrated on a CMOS integrated circuit.

14. The catheter of claim 1, wherein the capacitive micromachined ultrasound transducers are pre-collapsed capacitive micromachined ultrasound transducers.

15. A transurethral catheter comprising:
a shaft with distal and proximal ends, the distal end including:
a transducer module with a two-dimensional array of capacitive micromachined ultrasound transducers disposed onto a flexible material,
an integrated circuit configured to control an amplitude and power delivered to the capacitive micromachined ultrasound transducers of the array of capacitive micromachined ultrasound transducers to generate and adjustably focus an ultrasound beam to controllably heat a target zone; and
the integrated circuit further being configured to perform ultrasound imaging using the two-dimensional array of capacitive micromachined ultrasound transducers while concurrently controllably heating the target zone; and
a connector disposed at the proximal end, the connector connected with the integrated circuit by a power and data bus to provide electrical power and at least one focus control signal with instructions to at least one electronic processor to for controlling the adjustable focus at least by controlling the electrical power delivered to the at least one array of capacitive micromachined ultrasound transducers, the power and data bus being operably connected to the connector.

16. The catheter of claim 15, wherein the catheter further comprises a mechanical actuator configured to at least partially adjust the adjustable focus by deforming the transducer module.

17. A medical imaging system for acquiring medical image data from an imaging zone wherein the medical imaging system comprises:
a catheter, the catheter comprising,
a shaft with distal and proximal ends, wherein the distal end comprises a transducer module with at least one array of capacitive micromachined ultrasound transducers, the at least one array of capacitive micromachined ultrasound transducers having an adjustable focus for controllably heating a target zone, wherein the at least one array of capacitive micromachined ultrasound transducers is disposed on a flexible substrate, wherein the at least one array of capacitive micromachined ultrasound transducers is flexible,
a connector disposed at the proximal end, the connecter arranged to supply the at least one array of capacitive micromachined ultrasound transducers with electrical power, wherein the connector is arranged to supply at least one focus control signal to at least one electronic processor to control the adjustable focus, wherein the transducer module is partly flexible,
and the medical imaging system further comprising:
the processor programmed to control the medical image system and for controlling the adjustable focus of the catheter;
and the medical imaging system further comprising:
a memory containing machine executable instructions for execution by the processor, where execution of the instructions causes the processor to:
acquire the medical image data using the medical imaging system;
register a location of the distal end of the catheter in the medical image data;
generate focus control signals in accordance with the registered location of the distal end; and
control the focus using the catheter interface in accordance with the focus control signals, by at least partially adjusting the adjustable focus by deforming the transducer module at least by controlling the electrical power delivered to the at least one array of capacitive micromachined ultrasound transducers with a data bus operably connected to the connector.

18. The medical imaging system of claim 17, wherein the medical imaging system is any one of the following:
a magnetic resonance imaging system, a computed tomography system, and a diagnostic ultrasound system;

wherein the instructions further cause the processor to register a target zone of a subject in accordance with the medical image data; and wherein the instructions further cause the processor to generate focus control signals to control the focus such that the target zone is heated using the at least one array of capacitive micromachined ultrasound transducers.

19. The medical imaging system of claim 18, wherein execution of the instructions further causes the processor to:

acquire thermal imaging data using the medical imaging system; and reconstruct a thermal map using the thermal imaging data, wherein focus control signals are generated in accordance with the thermal map.

20. A non-transitory computer program product comprising machine executable instructions for execution by a processor of a medical imaging system for acquiring medical image data from an imaging zone, wherein the medical imaging system comprises a catheter interface for connecting to a catheter, the catheter comprising, a shaft with distal and proximal ends, wherein the distal end comprises a transducer module with at least one array of capacitive micromachined ultrasound transducers, the at least one array of capacitive micromachined ultrasound transducers having an adjustable focus for controllably heating a target zone, an integrated circuit configured to simultaneously drive a first portion of the capacitive micromachined ultrasound transducers at a first frequency to perform sonication and a second portion of the capacitive micromachined ultrasound transducers at a second frequency to perform imaging, a connector disposed at the proximal end, the connector arranged to supply the at least one array of capacitive micromachined ultrasound transducers with electrical power, wherein the connector is arranged to supply at least one focus control signal to at least one electronic processor to control the adjustable focus, wherein the transducer module is partly flexible, wherein execution of the instructions causes the processor to:

acquire the medical image data using the medical imaging system, register a location of the distal end of the catheter in the medical image data, generate focus control signals in accordance with the registered location of the distal end, control the focus using the catheter interface in accordance with the focus control signals by at least partially adjusting the adjustable focus by deforming the transducer module at least by controlling the electrical power delivered to the at least one array of capacitive micromachined ultrasound transducers with a data bus operably connected to the connector.

* * * * *